(12) United States Patent
Nakajima et al.

(10) Patent No.: US 10,322,997 B2
(45) Date of Patent: Jun. 18, 2019

(54) PHENYLDIFLUOROMETHYL-SUBSTITUTED PROLINAMIDE COMPOUND

(71) Applicant: ASTELLAS PHARMA INC., Chuo-ku (JP)

(72) Inventors: Yutaka Nakajima, Tokyo (JP); Sunao Imada, Tokyo (JP); Eriko Yamamoto, Tokyo (JP); Kazuyuki Tsuchiya, Tokyo (JP); Yu Harayama, Tokyo (JP); Shunichiro Matsumoto, Tokyo (JP)

(73) Assignee: ASTELLAS PHARMA INC., Chuo-ku (JP)

( * ) Notice: Subject to any disclaimer, the term of this patent is extended or adjusted under 35 U.S.C. 154(b) by 0 days.

(21) Appl. No.: 16/180,862

(22) Filed: Nov. 5, 2018

(65) Prior Publication Data

US 2019/0071398 A1     Mar. 7, 2019

Related U.S. Application Data

(63) Continuation of application No. PCT/JP2018/001927, filed on Jan. 23, 2018.

(30) Foreign Application Priority Data

Jan. 24, 2017  (JP) ................. 2017-010321

(51) Int. Cl.

| | |
|---|---|
| *C07D 401/10* | (2006.01) |
| *C07D 207/16* | (2006.01) |
| *C07D 403/10* | (2006.01) |
| *A61K 31/4439* | (2006.01) |
| *A61K 31/496* | (2006.01) |
| *A61P 37/06* | (2006.01) |
| *A61P 37/08* | (2006.01) |
| *A61P 13/12* | (2006.01) |

(52) U.S. Cl.
CPC ........ *C07D 207/16* (2013.01); *A61K 31/4439* (2013.01); *A61K 31/496* (2013.01); *A61P 13/12* (2018.01); *A61P 37/06* (2018.01); *A61P 37/08* (2018.01); *C07D 401/10* (2013.01); *C07D 403/10* (2013.01)

(58) Field of Classification Search
CPC ............... C07D 401/10; C07D 403/10; C07D 207/16
USPC .................................................. 514/254.01
See application file for complete search history.

(56) References Cited

FOREIGN PATENT DOCUMENTS

| | | |
|---|---|---|
| WO | 2010/121918 A1 | 10/2010 |
| WO | 2010/142650 A1 | 12/2010 |
| WO | 2012/059507 A1 | 5/2012 |
| WO | 2013/120921 A9 | 8/2013 |
| WO | 2014/029722 A1 | 2/2014 |
| WO | 2017/144483 A1 | 8/2017 |

OTHER PUBLICATIONS

Rupanagudi et al.-"Cathepsin S inhibition suppresses systemic lupus erythematosus and lupus nephritis because cathepsin S is essential for MHC class II-mediated CD4 T cell and B cell priming", *Ann Rheum Dis* 2015, vol. 74, pp. 452-463.
International Search Report and Written Opinion dated Apr. 9, 2018, issued in corresponding application PCT/JP2018/001927 (with partial English translation) (citing document AO).

*Primary Examiner* — Kahsay Habte
(74) *Attorney, Agent, or Firm* — Oblon, McClelland, Maier & Neustadt, L.L.P.

(57) ABSTRACT

Phenyldifluoromethyl-substituted prolinamide compounds that have a cathepsin S inhibitory effect, and are usable as active ingredients of pharmaceutical compositions for preventing and/or treating autoimmune diseases including systemic lupus erythematosus (SLE) and lupus nephritis, allergies, or graft rejection of an organ, bone marrow or tissue. Such compounds include (4R)—N-(1-cyanocyclopropyl)-4-(difluoro{4-[(4-methylpiperazin-1-yl)methyl]-2-(trifluoromethyl)phenyl}methyl)-1-[(1-methylcyclopropyl)carbonyl]-L-prolinamide, (4R)—N-(1-cyanocyclopropyl)-4-(difluoro{4-[(4-methylpiperazin-1-yl)methyl]-2-(trifluoromethyl)phenyl}methyl)-1-{[1-(trifluoromethyl)cyclopropyl]carbonyl}-L-prolinamide, (4R)—N-(1-cyanocyclopropyl)-4-[{4-[(4-ethylpiperazin-1-yl)methyl]-2-(trifluoromethyl)phenyl}(difluoro)methyl]-1-{[1-(trifluoromethyl)cyclopropyl]carbonyl}-L-prolinamide, (4R)—N-(1-cyanocyclopropyl)-4-[{4-[(4-ethylpiperazin-1-yl)methyl]-2-(trifluoromethyl)phenyl}(difluoro)methyl]-1-[(1-methylcyclopropyl)carbonyl]-L-prolinamide, and salts thereof.

6 Claims, No Drawings

PHENYLDIFLUOROMETHYL-SUBSTITUTED PROLINAMIDE COMPOUND

TECHNICAL FIELD

The present invention relates to a phenyldifluoromethyl-substituted prolinamide compound that has a cathepsin S inhibitory effect and is expected to be used as an active ingredient of a pharmaceutical composition, for example, a pharmaceutical composition for preventing and/or treating autoimmune disease including systemic lupus erythematosus (SLE) and lupus nephritis, allergies, or graft rejection of an organ, bone marrow or tissue.

BACKGROUND ART

Cathepsin S is a lysosomal cysteine protease expressed mainly in antigen-presenting cells such as dendritic cells, macrophages, and B cells, and is responsible for the degradation of the invariant chain bound to major histocompatibility complex class II (MHC class II) molecules at the time of generation. The MHC class II molecules bind to a self or non-self peptide incorporated extracellularly, and induces secretion of various cytokines by presenting the self peptide or the non-self peptide to CD4-positive T cells. It was confirmed that inhibition or deletion of the cathepsin S inhibits loading of an antigenic peptide to the MHC class II molecules, and furthermore, suppression of antigen presentation to the CD4-positive T cells lowers immune response against foreign antigens ("Immunity", 1999, vol. 10, No. 2, p. 207-217). It is considered that in a case of autoimmune disease such as SLE, the above-described antigen presentation occurs with respect to a pathogenic self peptide, and therefore it is considered that there is a high possibility of a cathepsin S inhibitor being useful for treating autoimmune disease ("Journal of Clinical Investigation", 1998, Vol. 101, No. 11, p. 2351-2363).

Accordingly, it is expected that the cathepsin S inhibitor is promising as an agent for preventing and/or treating autoimmune disease including SLE and lupus nephritis, or an agent for preventing and/or treating allergies, or graft rejection of an organ, bone marrow or tissue.

Patent Document 1 discloses that a compound of the formula (A) exhibits the cathepsin S inhibitory effect and is useful for treating various metabolic disease or immune disease such as SLE.

[Chem. 1]

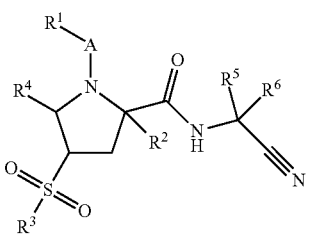

(A)

(Refer to this publication for the symbols in the formula.)

Patent Document 2 discloses that a compound of the formula (B) exhibits the cathepsin S inhibitory effect and is useful for treating various metabolic disease or immune disease such as SLE.

[Chem. 2]

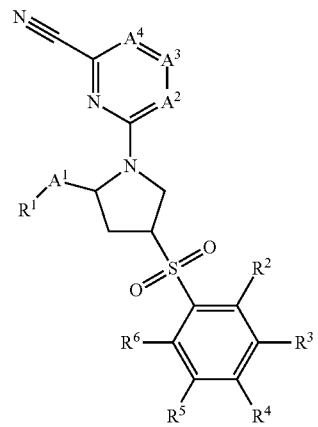

(B)

(Refer to this publication for the symbols in the formula.)

Non-Patent Document 1 discloses that a compound of the formula (C) interferes with the progression of SLE and lupus nephritis.

[Chem. 3]

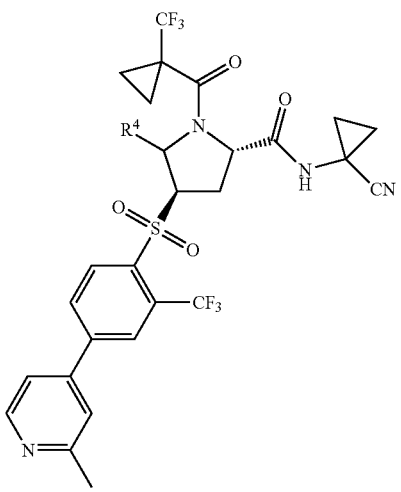

(C)

Patent Document 3 discloses that a compound of the formula (D) exhibits the cathepsin S inhibitory effect and is useful for treating diabetes and the like.

[Chem. 4]

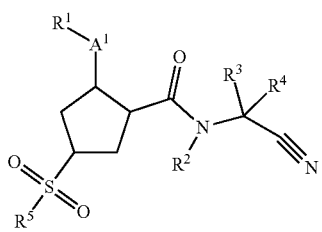

(D)

(Refer to this publication for the symbols in the formula.)

Patent Document 4 discloses that a compound of the formula (E) exhibits the cathepsin S inhibitory effect and is useful for treating diabetes and the like.

[Chem. 5]

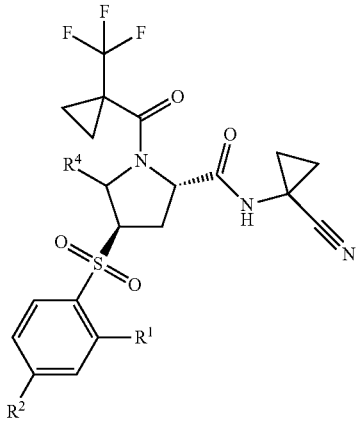

(E)

(Refer to this publication for the symbols in the formula.)

RELATED ART

Patent Document

[Patent Document 1] WO 2010/121918
[Patent Document 2] WO 2012/059507
[Patent Document 3] WO 2010/142650
[Patent Document 4] WO 2017/144483

Non-Patent Document

[Non-Patent Document 1] "Annals of the Rheumatic Diseases", 2015, Vol. 74, p. 452-463

DISCLOSURE OF INVENTION

Problems to Be Solved by the Invention

Provided is a compound that has a cathepsin S inhibitory effect and is expected to be useful as an active ingredient of a pharmaceutical composition, for example, a pharmaceutical composition for preventing and/or treating autoimmune disease including SLE and lupus nephritis, allergies, or graft rejection of an organ, bone marrow or tissue.

Means for Solving the Problems

As a result of intensive studies on the compound having the cathepsin S inhibitory effect, the inventors of the present invention have found that a phenyldifluoromethyl-substituted prolinamide compound has the cathepsin S inhibitory effect, thereby completing the present invention.

That is, the present invention relates to a compound of the formula (I) or a salt thereof, and relates to a pharmaceutical composition comprising the compound of the formula (I) or a salt thereof and one or more excipients.

[Chem. 6]

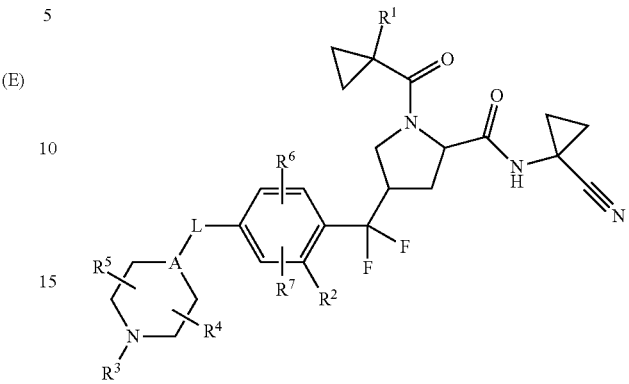

(I)

(In the formula,
$R^1$ is lower alkyl or halogeno-lower alkyl,
$R^2$ is a halogen or halogeno-lower alkyl,
L is a bond or —$CH_2$—,
A is CH or N,
$R^3$ is H or lower alkyl,
$R^4$ and $R^5$ are the same as or different from each other, and are H or lower alkyl, and
$R^6$ and $R^7$ are the same as or different from each other, and are H, lower alkyl, or a halogen.)

Unless described otherwise, in a case where symbols in the chemical formulae in the present specification are also used in other chemical formulae, the same symbols have the same meaning.

The present invention further relates to a pharmaceutical composition for preventing and/or treating autoimmune disease including SLE and lupus nephritis, allergies, or graft rejection of an organ, bone marrow or tissue, comprising the compound of the formula (I) or a salt thereof. The pharmaceutical composition includes an agent for preventing and/or treating autoimmune disease including SLE and lupus nephritis, allergies, or graft rejection of an organ, bone marrow or tissue, comprising the compound of the formula (I) or a salt thereof.

The present invention still further relates to:
(1) the compound of the formula (I) or a salt thereof, which is a cathepsin S inhibitor;
(2) the compound of the formula (I) or a salt thereof, for use as the cathepsin S inhibitor;
(3) the cathepsin S inhibitor comprising the compound of the formula (I) or a salt thereof;
(4) use of the compound of the formula (I) or a salt thereof for the manufacture of a pharmaceutical composition for preventing and/or treating autoimmune disease including SLE and lupus nephritis, allergies, or graft rejection of an organ, bone marrow or tissue;
(5) use of the compound of the formula (I) or a salt thereof for preventing and/or treating autoimmune disease including SLE and lupus nephritis, allergies, or graft rejection of an organ, bone marrow or tissue;
(6) the compound of the formula (I) or a salt thereof, for use in preventing and/or treating autoimmune disease including SLE and lupus nephritis, allergies, or graft rejection of an organ, bone marrow or tissue; and (7) a method for preventing and/or treating autoimmune disease including SLE and lupus nephritis, allergies, or graft rejection of an organ, bone marrow or tissue, the method comprising administering to a subject an effective amount of the compound of the formula (I) or a salt thereof.

The "subject" refers to humans or other animals in need of prevention or treatment of the disease, and in one embodiment, the subject refers to humans in need of prevention or treatment of the disease.

Effects of the Invention

The compound of the formula (I) or a salt thereof has the cathepsin S inhibitory effect, and can be used as an agent for preventing and/or treating autoimmune disease including SLE and lupus nephritis, allergies, or graft rejection of an organ, bone marrow or tissue.

EMBODIMENTS FOR CARRYING OUT THE INVENTION

Hereinafter, the present invention will be described in detail.

The term "lower alkyl" refers to a linear or branched alkyl having carbon atoms of 1 to 6 (hereinafter also referred to as $C_{1-6}$) such as methyl, ethyl, n-propyl, isopropyl, n-butyl, isobutyl, sec-butyl, tert-butyl, n-pentyl, and n-hexyl, and refers to $C_{1-4}$ alkyl in one embodiment, methyl or ethyl in one embodiment, and methyl in one embodiment.

The term "halogen" means F, Cl, Br, and I.

The term "halogeno-lower alkyl" is $C_{1-6}$ alkyl substituted with one or more halogens, and refers to $C_{1-6}$ alkyl substituted with 1 to 5 halogens in one embodiment and refers to $CF_3$ in one embodiment.

Some aspects of the present invention are shown below.

(1) A compound or a salt thereof, in which the formula (I) is represented by the following formula (Ia.).

[Chem. 7]

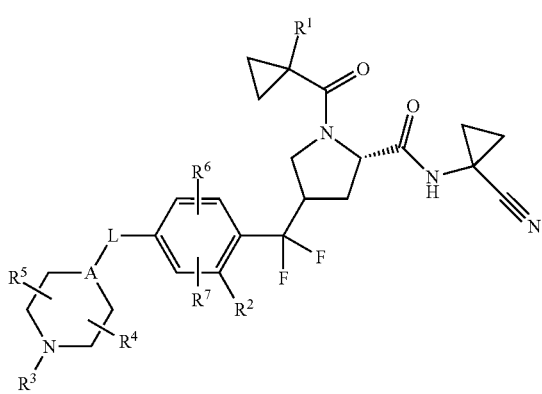

(2) A compound or a salt thereof, in which the formula (I) is represented by the following formula (Ib).

[Chem. 8]

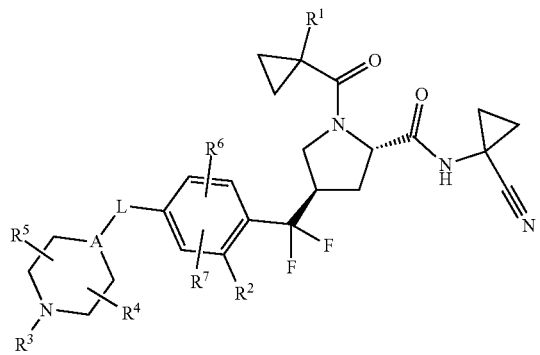

(3) A compound or a salt thereof, in which R' is lower alkyl or halogeno-lower alkyl; a compound or a salt thereof, in which R' is halogeno-lower alkyl; a compound or a salt thereof, in which R' is lower alkyl; a compound or a salt thereof, in which R' is methyl or $CF_3$; or a compound or a salt thereof, in which R' is methyl.

(4) A compound or a salt thereof, in which $R^2$ is a halogen or halogeno-lower alkyl; a compound or a salt thereof, in which $R^2$ is a halogen; a compound or a salt thereof, in which $R^2$ is halogeno-lower alkyl; or a compound or a salt thereof, in which $R^2$ is $CF_3$.

(5) A compound or a salt thereof, in which A is CH or N; a compound or a salt thereof, in which A is CH; or a compound or a salt thereof, in which A is N.

(6) A compound or a salt thereof, in which L is a bond or —$CH_2$—; a compound or a salt thereof, in which L is a bond; or a compound or a salt thereof, in which L is —$CH_2$—.

(7) A compound or a salt thereof, in which $R^3$ is H or lower alkyl; a compound or a salt thereof, in which $R^3$ is H; a compound or a salt thereof, in which $R^3$ is lower alkyl; a compound or a salt thereof, in which $R^3$ is methyl or ethyl; or a compound or a salt thereof, in which $R^3$ is methyl.

(8) A compound or a salt thereof, in which $R^4$ is H or lower alkyl; a compound or a salt thereof, in which $R^4$ is lower alkyl; or a compound or a salt thereof, in which $R^4$ is H.

(9) A compound or a salt thereof, in which $R^5$ is H or lower alkyl; a compound or a salt thereof, in which $R^5$ is lower alkyl; or a compound or a salt thereof, in which $R^5$ is H.

(10) A compound or a salt thereof, in which $R^6$ is H, lower alkyl, or a halogen; a compound or a salt thereof, in which $R^6$ is lower alkyl; a compound or a salt thereof, in which $R^6$ is a halogen; or a compound or a salt thereof, in which $R^6$ is H.

(11) A compound or a salt thereof, in which $R^7$ is H, lower alkyl, or a halogen; a compound or a salt thereof, in which $R^7$ is lower alkyl; a compound or a salt thereof, in which $R^7$ is a halogen; or a compound or a salt thereof, in which $R^7$ is H.

(12) A compound or a salt thereof which is represented by two or more non-contradictory combinations among the embodiments described in (1) to (11).

Examples of the compound or a salt thereof of the present invention represented by the combinations in the above embodiment (12) include the following embodiments.

(13) A compound of the formula (I) or a salt thereof, in which R' is lower alkyl or halogeno-lower alkyl, $R^2$ is a halogen or halogeno-lower alkyl, L is a bond or —$CH_2$—, A is CH or N, $R^3$ is H or lower alkyl, $R^4$ is H or lower alkyl, $R^5$ is H or lower alkyl, $R^6$ is H, and $R^7$ is H.

(14) A compound of the formula (Ia) or a salt thereof, in which R' is lower alkyl or halogeno-lower alkyl, $R^2$ is a halogen or halogeno-lower alkyl, L is a bond or —$CH_2$—, A is CH or N, $R^3$ is H or lower alkyl, $R^4$ is H or lower alkyl, $R^5$ is H or lower alkyl, $R^6$ is H, lower alkyl, or a halogen, and $R^7$ is H, lower alkyl, or a halogen.

(15) A compound of the formula (I) or a salt thereof, in which R' is lower alkyl or halogeno-lower alkyl, $R^2$ is a halogen or halogeno-lower alkyl, L is —$CH_2$—, A is CH or N, $R^3$ is H or lower alkyl, $R^4$ is H or lower alkyl, $R^5$ is H or lower alkyl, $R^6$ is H, lower alkyl, or a halogen, and $R^7$ is H, lower alkyl, or a halogen.

(16) A compound of the formula (I) or a salt thereof, in which R' is lower alkyl or halogeno-lower alkyl, $R^2$ is halogeno-lower alkyl, L is —$CH_2$—, A is N, $R^3$ is lower alkyl, $R^4$ is H, $R^5$ is H, $R^6$ is H, and $R^7$ is H.

(17) A compound of the formula (Ia) or a salt thereof, in which R' is lower alkyl or halogeno-lower alkyl, $R^2$ is halogeno-lower alkyl, L is —$CH_2$—, A is N, $R^3$ is lower alkyl, $R^4$ is H, $R^5$ is H, $R^6$ is H, and $R^7$ is H.

(18) A compound of the formula (Ib) or a salt thereof, in which R' is lower alkyl or halogeno-lower alkyl, $R^2$ is halogeno-lower alkyl, L is —$CH_2$—, A is N, $R^3$ is lower alkyl, $R^4$ is H, $R^5$ is H, $R^6$ is H, and $R^7$ is H.

Specific examples of the compounds included in the present invention include compounds or a salt thereof selected from the following group:

(4R)—N-(1-cyanocyclopropyl)-4-(difluoro{4-[(4-methylpiperazin-1-yl)methyl]-2-(trifluoromethyl)phenyl}methyl)-1-[(1-methylcyclopropyl)carbonyl]-L-prolinamide, (4R)—N-(1-cyanocyclopropyl)-4-(difluoro{4-[(4-methylpiperazin-1-yl)methyl]-2-(trifluoromethyl)phenyl}methyl)-1-{[1-(trifluoromethyl)cyclopropyl]carbonyl}-L-prolinamide, (4R)—N-(1-cyanocyclopropyl)-4-[{4-[(4-ethylpiperazin-1-yl)methyl]-2-(trifluoromethyl)phenyl}(difluoro)methyl]-1-{[1-(trifluoromethyl)cyclopropyl]carbonyl}-L-prolinamide, and (4R)—N-(1-cyanocyclopropyl)-4-[{4-[(4-ethylpiperazin-1-yl)methyl]-2-(trifluoromethyl)phenyl}(difluoro)methyl]-1-[(1-methylcyclopropyl)carbonyl]-L-prolinamide.

Specific examples of the compounds included in the present invention include a compound or a salt thereof, which is a crystal containing (4R)—N-(1-cyanocyclopropyl)-4-(difluoro{4-[(4-methylpiperazin-1-yl)methyl]-2-(trifluoromethyl)phenyl}methyl)-1-[(1-methylcyclopropyl)carbonyl]-L-prolinamide (hereinafter, referred to as "Compound A" in some cases) and succinic acid in a molar ratio of 1:2, and which is characterized by any one of the following aspects.

(1) The compound has peaks near 2θ(°) 2.7, 5.3, 9.8, 10.4, 13.5, 14.0, 15.1, 16.6, 17.4, and 24.4 by powder X-ray diffraction.

(2) The compound characteristically has peaks near 2θ(°) 5.3, 9.8, 15.1, 16.6, and 24.4 by powder X-ray diffraction.

(3) The compound has an endothermic peak near 134.3° C. by differential scanning calorimetry (DSC analysis).

The crystal containing Compound A and succinic acid in a molar ratio of 1:2 also include a crystal of a disuccinate of Compound A, and a co-crystal of a succinic acid and a monosuccinate of Compound A.

Tautomers and geometric isomers may exist in the compound of the formula (I) depending on the types of the substituent. In the present specification, the compound of the formula (I) may be described in only one form of an isomer, but the present invention also includes isomers other than that, and includes a form obtained by separating isomers, or a mixture thereof.

In addition, the compound of the formula (I) may have an asymmetric center or an axis chirality in some cases, and enantiomers (optical isomers) based thereon may exist. The compound of the formula (I) or a salt thereof includes any of an isolated individual enantiomer such as (R) form or (S) form, and a mixture thereof (including a racemic mixture or a non-racemic mixture). In one embodiment, the enantiomer is "stereochemically pure". The term "stereochemically pure" refers to a degree of purity that those skilled in the art can recognize that an enantiomer is substantially stereochemically pure. In another embodiment, the enantiomer is, for example, a compound having stereochemical purity of 90% ee (enantiomeric excess) or more, 95% ee or more, 98% ee or more, or 99% ee or more.

The salt of the compound of the formula (I) is a pharmaceutically acceptable salt of the compound of the formula (I), and depending on the types of substituents, an acid addition salt may be formed in some cases. Specific examples thereof include an acid addition salt of inorganic acid such as hydrochloric acid, hydrobromic acid, hydroiodic acid, sulfuric acid, nitric acid, and phosphoric acid; and organic acid such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid, and the like. In addition, the salt of the compound of the formula (I) also include a co-crystal of the compound of the formula (I) and an acid.

The present invention further includes substances having crystalline polymorphism, various hydrates and solvates of the compound of the formula (I) and a salt thereof. The present invention still further includes the compound of the formula (I) or a salt thereof, which is pharmaceutically acceptable and is labeled with one or more radioactive or non-radioactive isotopes. Examples of suitable isotopes used for isotopic labeling of the compound of the present invention include isotopes such as hydrogen ($^2H$, $^3H$, and the like), carbon ($^{11}C$, $^{13}C$, $^{14}C$, and the like), nitrogen ($^{13}N$, $^{15}N$, and the like), oxygen ($^{15}O$, $^{17}O$, $^{18}O$, and the like), fluorine ($^{18}F$ and the like), chlorine ($^{36}Cl$ and the like), iodine ($^{123}I$, $^{125}I$, and the like), phosphorus ($^{32}P$ and the like), and sulfur ($^{35}S$ and the like).

The isotope-labeled compound of the present invention can be used for research and the like on tissue distribution of drugs and/or substrates. For example, radioactive isotopes such as tritium ($^3H$) and carbon 14 ($^{14}C$) can be used for this purpose from the viewpoint of the ease of labeling and the convenience of detection.

Substitution by heavier isotopes, for example, substitution of hydrogen by deuterium ($^2H$), is advantageous in terms of treating by improving metabolic stability in some cases (for example, increase in in vivo half-life, decrease in required dose, decrease in interaction between drugs).

Substitution by positron emission isotopes ($^{11}$C, $^{18}$F, $^{15}$O, $^{13}$N, and the like) can be used in a positron-emission tomography (PET) test for testing occupancy of a substrate receptor.

The isotope-labeled compound of the present invention can be generally produced by methods of the related art known to those skilled in the art, or by the same preparation method as in examples or preparation examples by using suitable reagents which is isotopic labeled in place of unlabeled reagents.

(Preparation Method)

The compound of the formula (I) and a salt thereof can be produced by applying various known synthetic methods using the basic structure thereof or the characteristics based on the types of substituents. Depending on the types of functional groups, it is effective for production technique in some cases, to replace the functional group with an appropriate protective group (a group which can be easily converted to the functional group) in advance at a stage from a starting material to an intermediate. Examples of such a protective group include a protective group and the like described in "Greene's Protective Groups in Organic Synthesis (4th edition, 2006)" by Wuts (P. G. M. Wuts) and Greene (T. W. Greene). The protective group may be appropriately selected and used according to these reaction conditions. In such a method, a desired compound can be obtained by introducing the protective group to carry out the reaction, and then removing the protective group if necessary.

A pharmaceutically acceptable prodrug is a compound having a group that can be converted into an amino group, a hydroxyl group, a carboxyl group, or the like by solvolysis or under physiological conditions. Examples of a group forming the prodrug include a group described in Prog. Med., 5, 2157-2161 (1985) and "Pharmaceutical Research and Development, Drug Design, Hirokawa Publishing Company" (Hirokawa-Shoten Ltd., 1990), Vol. 7, Molecular Design 163-198.

In addition, similarly to the protective group, a prodrug of the compound of the formula (I) can be produced by introducing a specific group at a stage from a starting material to an intermediate, or further carrying out the reaction using the obtained compound of the formula (I). The reaction can be carried out by applying a method known to those skilled in the art, such as general esterification, amidation, and dehydration.

Hereinafter, a representative method for preparing the compound of the formula (I) is described. Each preparation method can also be carried out with reference to the reference document attached to the explanation. The preparation method of the present invention is not limited to the examples shown below.

In the present specification, the following abbreviations may be used.

DMF=N,N-dimethylformamide, DMSO=dimethyl sulfoxide, EtOAc=ethyl acetate, MeO H=methanol, MeCN=acetonitrile, THF=tetrahydrofuran, TEA=triethylamine, DIPEA=N,N-diisopropylethylamine, NMM=N-methylmorpholine, XPhos=2-dicyclohexylphosphino-2',4',6'-triisopropylbiphenyl, RuPhos=2-dicyclohexylphosphino-2',6'-diisopropoxybiphenyl, XantPhos=4,5-bis(diphenylphosphino)-9,9-dimethylxanthene, HATU=O-(7-azabenzotriazol-1-yl)-N,N,N',N'-tetramethyluronium hexafluorophosphate, brine=saturated sodium chloride aqueous solution, MgSO$_4$=anhydrous magnesium sulfate.

In the structural formulae and groups in the present specification, the following abbreviations may be used.

Ac=acetyl, BOC=tert-butoxycarbonyl, t-Bu=tert-butyl, Me=methyl, Et=ethyl, CF$_3$=trifluoromethyl, Ms=methanesulfonyl, Ts=p-toluenesulfonyl, Tf=trifluoromethanesulfonyl, Ph=phenyl.

(Preparation Method 1)

[Chem. 9]

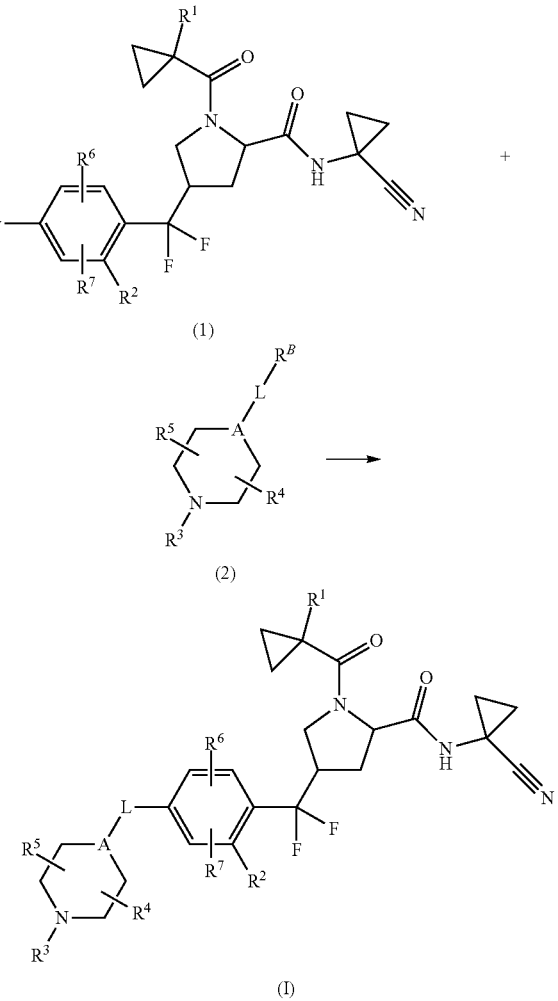

(In the formula, R$^B$ represents —BF$_3$$^-$Y$^+$, —B(OR)$_3$, and the like. Lv represents a leaving group. Y represents an alkali metal such as Na or K. R may be H or lower alkyl, or two Rs may form lower alkylene together.)

The compound of the formula (I) can be obtained by a coupling reaction between Compound (1) and Compound (2). Examples of the leaving group include a halogen, TfO, and the like.

In this reaction, Compound (1) and Compound (2) are used in equivalent amounts, or either thereof in an excess amount. A mixture thereof is stirred in a solvent inert during the reaction in the presence of a base and a palladium catalyst at room temperature to heating under reflux, in one embodiment, from room temperature to 150° C., usually for 0.1 hours to 5 days.

Examples of the solvent include, but are not particularly limited to, aromatic hydrocarbons such as toluene, ethers such as THF and 1,4-dioxane, halogenated hydrocarbons such as dichloromethane, alcohols, DMF, DMSO, EtOAc, MeCN, H$_2$O, and a mixed solvent thereof. As examples of the base, an inorganic base such as Cs$_2$CO$_3$, K$_3$PO$_4$, K$_2$CO$_3$, Na$_2$CO$_3$, and KOH is preferable. Examples of the palladium catalyst include a palladium catalyst adjusted in the system by palladium acetate and a phosphine ligand such as XPhos and RuPhos, tetrakis(triphenylphosphine)palladium, dichlorobis(triphenylphosphine)palladium, 1,1'-bis(diphenylphosphino)ferrocene-palladium(II) dichloride, and the like.

[Document]

Edited by A. d. Meijere and F. Diederich, "Metal-Catalyzed Cross-Coupling Reactions", 1$^{st}$ edition, VCH Publishers Inc., 1997

Edited by The Chemical Society of Japan, "5$^{th}$ Edition, Courses in Experimental Science (Vol. 14)", Maruzen, 2005

(Preparation Method 2)

[Chem. 10]

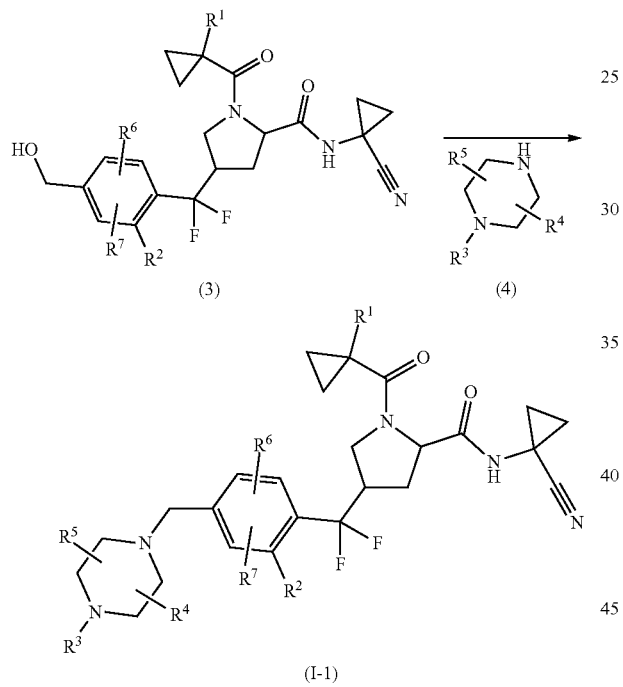

(In the formula, the compound of the formula (I-1) is the compound of the formula (I) in which L is CH$_2$ and A is N.)

The compound of the formula (I-1) can be obtained by introducing a leaving group to Compound (3), and then allowing the reaction with Compound (4).

In this reaction, a compound obtained by allowing the reaction of Compound (3) with a halogenated sulfonyl compound such as MsCl or TsCl in a solvent inert during the reaction in the presence of a base, and Compound (4) are used in equivalent amounts, or either thereof in an excess amount. A mixture thereof is stirred in a solvent inert during the reaction in the presence of a base under ice cooling to heating under reflux, preferably at 0° C. to 120° C., usually for 0.1 hours to 5 days.

Examples of the solvent include, but are not particularly limited to, aromatic hydrocarbons such as toluene, ethers such as 1,4-dioxane, halogenated hydrocarbons such as dichloromethane, DMF, DMSO, EtOAc, MeCN, and a mixed solvent thereof. Examples of the base include an organic base such as TEA, DIPEA, and NMM, an inorganic base such as K$_2$CO$_3$, Na$_2$CO$_3$, and KOH, and the like.

(Preparation Method 3)

[Chem. 11]

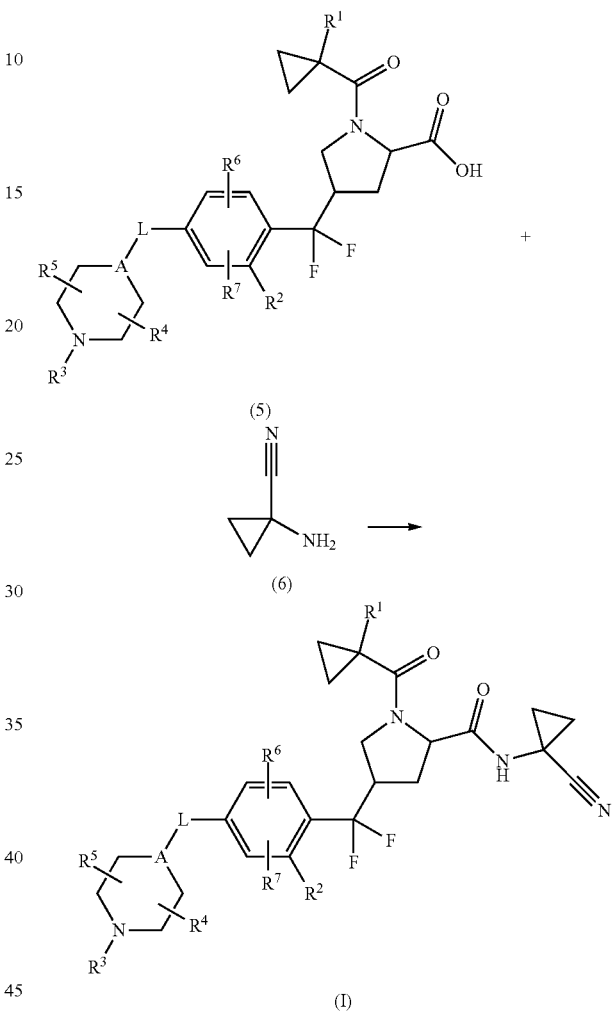

The compound of the formula (I) can be obtained by an amidation reaction between Compound (5) and Compound (6). In this reaction, Compound (5) and Compound (6) are used in equivalent amounts, or either thereof in an excess amount. A mixture thereof is stirred in a solvent inert during the reaction in the presence of a condensing agent under cooling to heating, preferably at −20° C. to 60° C., usually for 0.1 hours to 5 days. Examples of the solvent include, but are not particularly limited to, aromatic hydrocarbons such as toluene, ethers such as THF and 1,4-dioxane, halogenated hydrocarbons such as dichloromethane, alcohols, DMF, DMSO, EtOAc, MeCN, and a mixed solvent thereof. Examples of the condensing agent include HATU, 1-(3-dimethylaminopropyl)-3-ethylcarbodiimide or a hydrochloride thereof, dicyclohexylcarbodiimide, 1,1'-carbonyldiimidazole, diphenylphosphoryl azide, and the like. In some cases, it is preferable to use an additive (for example, 1-hydroxybenzotriazole) for the reaction. In some cases, it is advantageous to carry out the reaction in the presence of an organic base such as TEA, DIPEA, and NMM, or an inorganic base such as $K_2CO_3$, $Na_2CO_3$, and KOH, and the like in order to allow the reaction to proceed smoothly.

Furthermore, a method in which Compound (5) is converted into a reactive derivative, and then the reaction with Compound (6) is allowed can be used. Examples of the reactive derivative of a carboxylic acid include an acid halide obtained by reaction with a halogenating agent such as phosphorus oxychloride and thionyl chloride, a mixed acid anhydride obtained by reaction with isobutyl chloroformate or the like, an active ester obtained by condensing with 1-hydroxybenzotriazole or the like, and the like. The reaction between these reactive derivatives and Compound (6) is carried out in a solvent inert during the reaction, such as halogenated hydrocarbons, aromatic hydrocarbons, ethers, or the like under cooling to heating, preferably at $-20°$ C. to $60°$ C.

[Document]

S. R. Sandler and W. Karo, "Organic Functional Group Preparations", $2^{nd}$ Edition, Vol. 1, Academic Press, Inc., 1991

Edited by The Chemical Society of Japan, "Courses in Experimental Chemistry ($5^{th}$ Edition)", Vol. 16 (2005) (Maruzen)

(Starting Material Synthesis 1)

[Chem. 12]

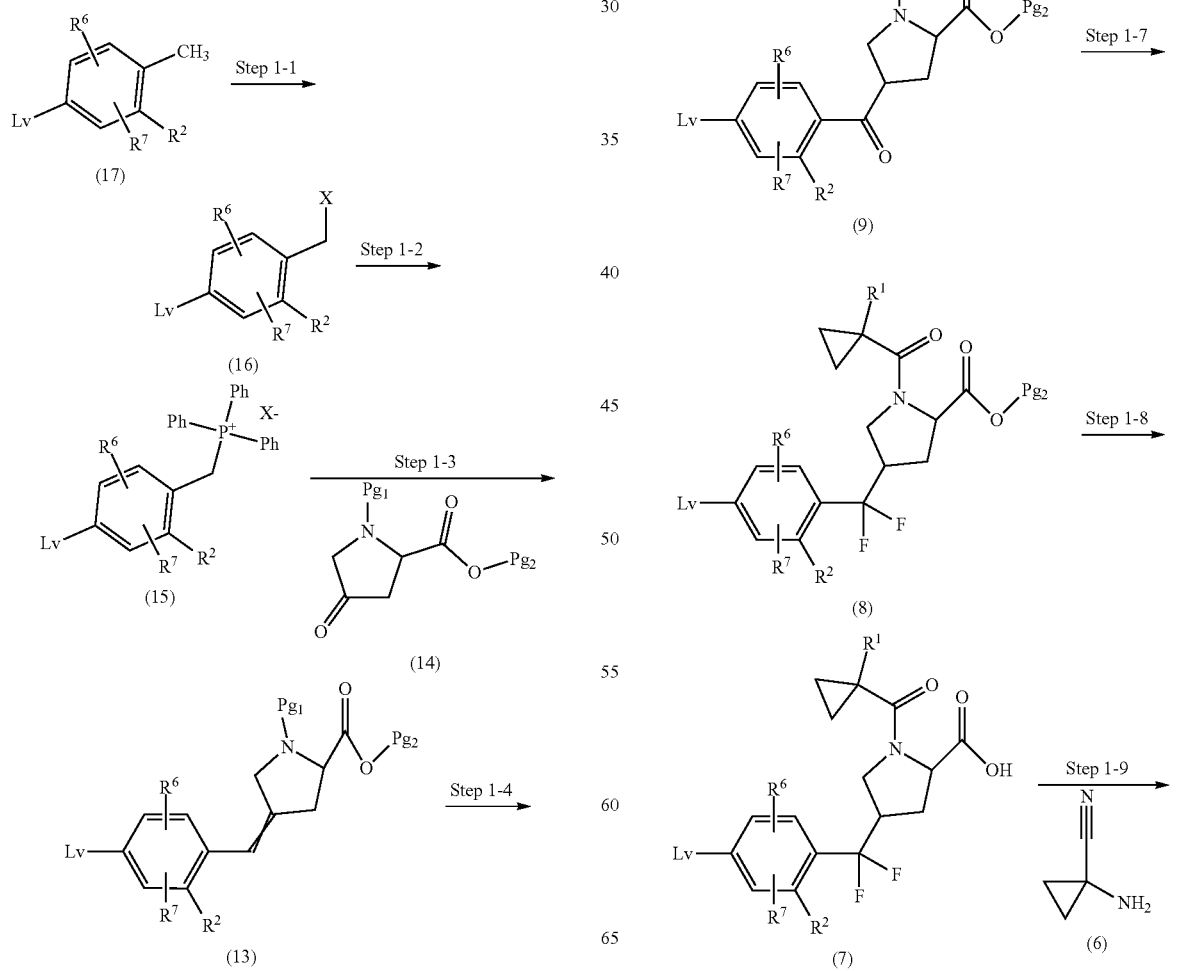

-continued

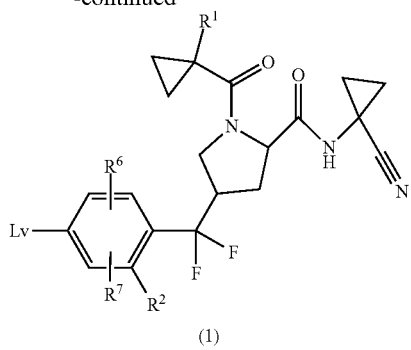

(1)

(In the formula, Lv is a leaving group, $P_{g1}$ and $P_{g2}$ are protective groups, and X is a halogen. Crossed double bonds in Compound (13) represent a mixture of geometric isomers.)

Examples of $P_{g1}$ include a BOC group and the like, and examples of $P_{g2}$ include a t-Bu group, an Et group, a Me group, and the like.

Steps represented by Step 1-1 to Step 1-3 are a reaction for obtaining Compound (15) used as a Wittig reagent (phosphorus ylide) from Compound (17), and a reaction for obtaining Compound (13) by the Wittig reaction of Compound (15) and Compound (14), respectively. In Step 1-1 and Step 1-2, Compound (17) is allowed to react with a halogenating agent such as N-bromosuccinimide or bromine so to form Halide (16), and then a mixture with triphenylphosphine is stirred in a solvent inert during the reaction under cooling to heating under reflux, in one embodiment, at 0° C. to 120° C., usually for 0.1 hours to 5 days. In a case of being dihalogenated during the halogenation reaction, Monohalide (16) can be obtained by reacting with diethyl phosphonate. In Step 1-3, a mixture of Compound (14) and Compound (15) is stirred in a solvent inert during the reaction in the presence of a base under cooling to heating under reflux, preferably at 0° C. to 100° C., usually for 0.1 hours to 10 days. Examples of the solvent include aromatic hydrocarbons, ethers, halogenated hydrocarbons such as dichloromethane, alcohols, DMF, DMSO, EtOAc, MeCN, and a mixture thereof. Examples of the base include an organic base such as sodium methoxide, potassium tert-butoxide, n-butyl lithium, lithium hexamethyldisilazide, an inorganic base such as $K_2CO_3$, $Na_2CO_3$, and KOH, and the like.

[Document]
Wittig, G. et al., U. Ber., 1954, Vol. 87, p. 1318

A step represented by Step 1-4 is a reaction for obtaining Compound (12) by oxidation reaction that occurs after hydroboration of alkene of Compound (13). In this reaction, a reactant which is obtained by stirring a mixture of Compound (13) and a borane-THF complex, 9-borabicyclo[3.3.1]nonane, disiamylborane, thexylborane, or the like in a solvent inert during the reaction, preferably at 10° C. to 80° C. usually for 0.1 hours to 3 day is processed with an equivalent amount or an excess amount of an oxidizing agent in a solvent inert during the reaction in the presence of a base under cooling to heating under reflux, preferably at −20° C. to 80° C., usually for 0.1 hours to 3 days, and thereby Compound (12) can be obtained.

Examples of the solvent include aromatic hydrocarbons, ethers such as THF, halogenated hydrocarbons, DMF, DMSO, EtOAc, MeCN, and a mixture thereof. Examples of the base include NaOH, $K_2CO_3$, $Na_2CO_3$, and KOH, and the like. Examples of the oxidizing agent include hydrogen peroxide, cumene hydroperoxide, peracetic acid, perbenzoic acid, m-chloroperbenzoic acid, oxone, activated manganese dioxide, chromic acid, potassium permanganate, sodium periodate, and the like.

[Document]
J. Am. Chem., Soc., 1956, Vol. 78, p. 5694-5695
J. Org. Chem., 1986, Vol. 51, p. 439-445

A step represented by Step 1-5 is a reaction for obtaining Compound (11) by the oxidation reaction of Compound (12). In this reaction, Compound (12) is processed with an equivalent amount or an excess amount of an oxidizing agent, in a solvent inert during the reaction under cooling to heating, preferably at −20° C. to 80° C., usually for 0.1 hours to 3 days. In this reaction, DMSO oxidation such as tetrapropylammonium perruthenate (TPAP) oxidation, or Swern oxidation, or oxidation using Dess-Martin reagent is suitably used. In the TPAP oxidation, Compound (12) is processed in the presence of tetrapropylammonium perruthenate which is an oxidation catalyst, molecular sieve 4A which is a dehydrating agent, and N-methylmorpholin-N-oxide (NMMO) which is a reoxidant. Examples of the solvent include aromatic hydrocarbons, ethers, halogenated hydrocarbons such as dichloromethane, DMF, DMSO, EtOAc, MeCN, and a mixture thereof. Examples of other oxidizing agents include hydrogen peroxide, cumene hydroperoxide, peracetic acid, perbenzoic acid, m-chloroperbenzoic acid, oxone, activated manganese dioxide, chromic acid, potassium permanganate, sodium periodate, and the like.

[Document]
J. Chem. Soc., Chem. Commun., 1987, p. 1625-1627
Edited by The Chemical Society of Japan, "5th Edition, Courses in Experimental Science (Vol. 14)", Maruzen, 2005

A step represented by Step 1-6 is a reaction for deprotecting the protective group $P_{g1}$ of Compound (11) and then condensing with Compound (10), and thereby obtaining Compound (9). The step can be carried out in the same manner as in Preparation Method 3 after carrying out deprotection reaction with reference to the method described in "Greene's Protective Groups in Organic Synthesis", 4th edition, 2006, and the like.

A step represented by Step 1-7 is a reaction for obtaining Compound (8) by fluorination of Compound (9). In this reaction, Compound (9) is stirred in a solvent inert during the reaction in the presence of a fluorinating agent under cooling to heating, preferably at −20° C. to 120° C., usually for 0.1 hours to 10 days. Examples of the solvent include aromatic hydrocarbons, ethers, halogenated hydrocarbons such as dichloromethane, DMF, DMSO, EtOAc, MeCN, and a mixture thereof. Examples of the fluorinating agent include 4-tert-butyl-2,6-dimethylphenylsulfur trifluoride, hydrogen fluoride, diethylaminosulfur trifluoride (DAST), sulfur tetrafluoride ($SF_4$), bis(2-methoxyethyl)aminosulfur trifluoride, and the like.

[Document]
J. Am. Chem. Soc., 2010, Vol. 132, p. 18199-18205

A step represented by Step 1-8 is a reaction for obtaining Compound (7) by deprotection of Compound (8). This reaction can be referred to, for example, the method described in "Greene's Protective Groups in Organic Synthesis", 4th edition, 2006, and the like.

A step represented by Step 1-9 is a reaction for obtaining Compound (1) by condensing Compound (7) and Compound (6). The step can be carried out by the same method as Preparation Method 3.

(Starting Material Synthesis 2)

[Chem. 13]

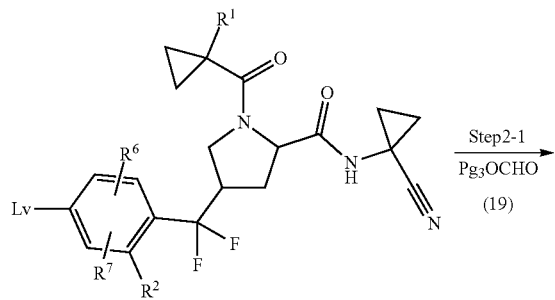

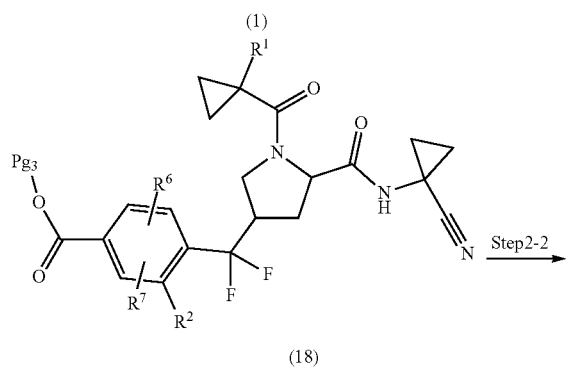

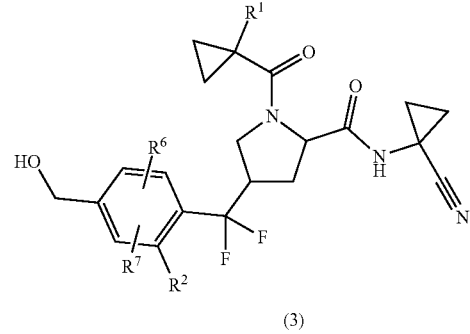

(In the Formula, $P_{g}3$ Represents a Protective Group.)
Examples of $P_{g3}$ include 2,4,6-trichlorophenyl.

A step represented by Step 2-1 is a reaction for obtaining Compound (18) by the reaction between Compound (1) and Compound (19). The step can be carried out in the same method as Preparation Method 1 except that Compound (19) is used in place of Compound (2).

As the solvent, toluene or benzotrifluoride is preferable. As the base, TEA or tributylamine is preferable. As the palladium catalyst, a palladium catalyst adjusted in situ by palladium acetate and a phosphine ligand such as XantPhos is preferable.

[Document]
Organic Letters, 2012, Vol. 14, No. 20, pp. 5370-5373.

A step represented by Step 2-2 is a reaction for obtaining Compound (3) by the reduction reaction of Compound (18). In this reaction, Compound (18) is processed with an equivalent amount or an excess amount of a reducing agent, in a solvent inert during the reaction under cooling to heating, preferably at −20° C. to 80° C., usually for 0.1 hours to 3 hours. Examples of the solvent include aromatic hydrocarbons, ethers, halogenated hydrocarbons, alcohols such as MeOH, DMF, DMSO, EtOAc, MeCN, and a mixture thereof. Examples of the reducing agent include hydride reducing agents such as sodium borohydride and lithium borohydride.

[Document]
M. Hudlicky, "Reductions in Organic Chemistry, $2^{nd}$ Edition (ACS Monograph: 188)," ACS, 1996
R. C. Larock, "Comprehensive Organic Transformations", $2^{nd}$ Edition, VCH Publishers, Inc., 1999
T. J. Donohoe "Oxidation and Reduction in Organic Synthesis (Oxford Chemistry Primers 6)", Oxford Science Publications, 2000
Edited by The Chemical Society of Japan, "Courses in Experimental Chemistry ($5^{th}$ Edition)", Vol. 14 (2005) (Maruzen)

(Starting Material Synthesis 3)

[Chem. 14]

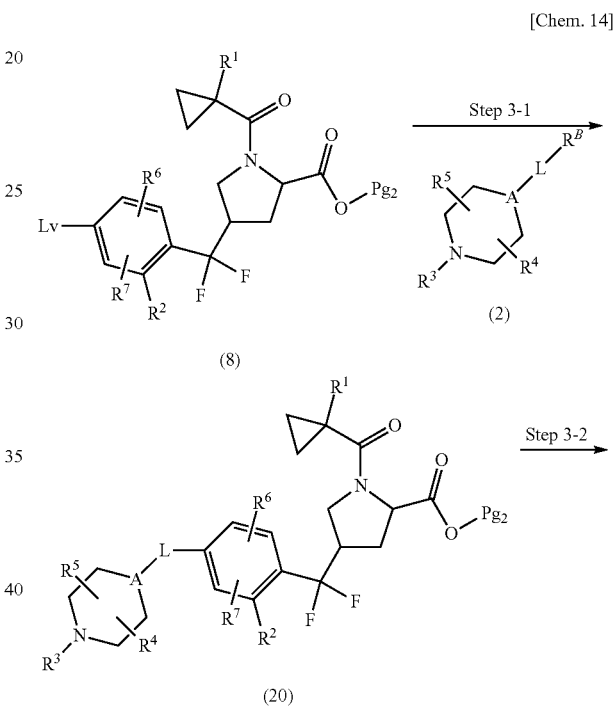

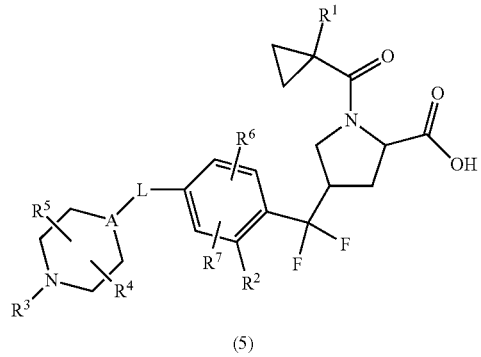

A step shown in Step 3-1 is a reaction for obtaining Compound (20) by a coupling reaction between Compound (8) and Compound (2), and can be carried out by the same method as in Preparation Method 1.

A step represented by Step 3-2 is a reaction for obtaining Compound (5) by deprotection of Compound (20), and can be carried out by the same method as Step 1-8 of Starting Material Synthesis 1.

The compound of the formula (I) is isolated as a free form compound, a salt thereof, a hydrate, a solvate, or a substance having crystalline polymorphism, and purified. The salt of the compound of the formula (I) can also be prepared by subjecting the compound to a salt formation reaction of a general method.

Isolation and purification are carried out by applying usual chemical operations such as extraction, fractional crystallization, and various fractionation chromatography.

Various isomers can be prepared by selecting an appropriate starting compound or can be separated by using a difference in physicochemical properties between isomers. For example, the optical isomer can be obtained by a general optical resolution method of racemic form (for example, fractional crystallization leading to a diastereomeric salt with an optically active base or an acid, chromatography using a chiral column or the like, and the like), or can be prepared from an appropriate optically active starting compound.

The pharmacological activity of the compound of the formula (I) can be confirmed by the following tests or well-known improved tests.

Test Example 1: Measurement of in Vitro Human Cathepsin S Inhibitory Activity

To a 96-well plate, 5 µL of human cathepsin S enzyme (R&D 1183-CY-010) was added so as to be 20 ng/well. Next, with assay buffer (50 mM sodium acetate, 250 mM sodium chloride, and 5 mM dithiothreitol (DTT), pH=4.5), a test compound (10 mM DMSO solution) was diluted 10-fold dilution series with 5 steps so that a final concentration becomes 0.1 nM to 1 µM or diluted 3-fold dilution series with 7 steps so that a final concentration becomes 0.01 nM to 10 nM, and 10 µL thereof was added to the well (final DMSO concentration was 0.1%), followed by addition of 25 µL of synthetic substrate VVR-AMC (Peptide Institute 3211-V) so that a final concentration becomes 40 µM, and thereby an enzymatic reaction was initiated. The fluorescence intensity (excitation wavelength: 380 nm, fluorescence wavelength: 460 nm) was measured at 37° C. for 5 to 10 minutes from the start of the reaction using a spectrofluorophotometer (SPECTRAMAX GEMINI, Molecular Devices), and a reaction rate when linearity was recognized (5 minutes) was obtained for each concentration of the test compound. An inhibition rate at each concentration was defined by suppressing a reaction rate at the time of non-addition of an enzyme without adding the test compound and a reaction rate at the time of addition of an enzyme without adding the test compound by 100% inhibition and 0% inhibition, respectively, and therefore an $IC_{50}$ value was calculated by a sigmoid Emax nonlinear regression method. The results are shown in Table 1. In the table, Ex represents Example compound No., and Dat1 represents the $IC_{50}$ value (nM) of human cathepsin S inhibitory activity.

TABLE 1

| Ex | Dat1 |
|---|---|
| 2 | 0.81 |
| 4 | 1.0 |
| 8 | 0.88 |
| 13 | 1.0 |
| 14 | 0.43 |

Test Example 2: Evaluation of Inhibitory Effect on in Vitro MHC Class II Expression Using Mouse Splenocytes (Cell Evaluation System)

In antigen-presenting cells, inhibition of cathepsin S suppresses expression of MHC class II molecules. As a result, suppression of antigen presentation to CD4-positive T cells causes a deterioration in the immune response to foreign antigens. In regard to an increase in MHC class II expression in B cells, the inhibitory effect of the compound of the formula (I) was examined.

Splenocytes collected from male C57BL/6J mice (Charles River Laboratories Japan, Inc.) were seeded in a 96-well plate by $1\times10^5$ cells/well. With RPMI 1640 medium (containing 10% fetal bovine serum (FCS), $5\times10^{-5}$ M 2-mercaptoethanol, 50 IU/mL penicillin, and 50 µg/mL streptomycin), 10 mM DMSO solution of the test compound was diluted 5-fold dilution series with 9 steps so that a final concentration becomes 0.026 nM to 10 µM, or diluted 5-fold dilution series with 12 steps so that a final concentration becomes 0.205 pM to 10 µM (final DMSO concentration is 0.1%), and added. At the same time, LPS (Sigma L4005) was added to the well so that the final concentration becomes 2 µg/mL, and the cells were cultured at 37° C. under 5% $CO_2$ for 48 hours. After culturing, the cells were stained with biotin-labeled YAe antibody (EBIOSCIENCE 13-5741-85) at 4° C. for 20 minutes, and washed. The cells were further stained with FITC fluorochrome labeled anti-mouse B220 antibody (BD BIOSCIENCES 553088) and PE fluorochrome labeled streptavidin (BD BIOSCIENCES 554061) for 20 minutes at 4° C. Therefore, an expression level (fluorescence intensity of YAe-biotin/streptavidin-PE) of MHC class II bound to the Ea peptide in B220 positive B cells was measured by using a flow cytometry system (Guava EasyCyte Plus System, Millipore). An inhibition rate at each concentration was defined by suppressing a value at the time of non-stimulation of LPS without addition of the test compound and a value at the time of stimulation of LPS without addition of the test compound by 100% inhibition and 0% inhibition, respectively, and therefore an $IC_{50}$ value was calculated by the sigmoid Emax nonlinear regression method. The results are shown in Table 2. In the table, Ex represents Example compound No., and Dat2 represents the $IC_{50}$ value (nM).

TABLE 2

| Ex | Dat2 |
|---|---|
| 2 | 0.65 |
| 4 | 0.62 |
| 8 | 0.59 |
| 13 | 0.37 |
| 14 | 0.60 |

Test Example 3: Evaluation of Ex Vivo MHC Class II Expression Inhibitory Effect Using Mouse Peripheral Blood The expression inhibitory effect of MHC class II molecules was evaluated in an ex vivo system.

The test compound was orally administered to male C57BL/6J mice (Charles River Laboratories Japan, Inc.), and an inhibition effect with respect to an increase in the expression of MHC class II in B cells of peripheral blood after oral administration was examined. That is, 10 mL/kg of the test compound dissolved in a vehicle [30% propylene glycol solvent {propylene glycol: hydrogenated castor oil (HCO40): Tween 80=4:2:1}/HCl (2 equivalents to the test compound)/water] was orally administered to male C57BL/6J mice (dose: 0.3 mg/kg, 4 subjects per group), and peripheral blood was recovered after 6 hours. To 90 μL of the peripheral blood, 10 μL of PBS or 10 μL (final concentration 100 μg/mL) of LPS (Sigma L4005) was added, and the culturing was carried out at 37° C. under 5% $CO_2$ for 15 hours. After culturing, the cells were stained with FITC fluorochrome labeled anti-mouse I-A/I-E antibody (BD BIOSCIENCES 553623) and PE fluorochrome labeled anti-mouse B220 antibody (BD BIOSCIENCES 553090) for 30 minutes under refrigeration, and then hemolysis and fixation were carried out for 11 to 12 minutes at 37° C. using a buffer (BD BIOSCIENCES Phosflow Lyse/Fix Buffer 558049). After washing, using the flow cytometry system (FACSCanto II, BD BIOSCIENCES), an expression level of MHC class II on a surface of B220 positive B cells was measured with an average fluorescence intensity of FITC (hereinafter referred to as MFI) as an index. A difference between MFI of LPS stimulation and MFI of no stimulation was defined as ΔMFI, and therefore, an inhibition rate of ΔMFI according to the administration of the test compound was calculated by setting ΔMFI of mice administered with 10 mL/kg of the vehicle to 1.

In this test, the compound of Example 8 showed 41% inhibition (0.3 mg/kg), which inhibited the increase in expression of MHC class II.

Test Example 4: Evaluation of Inhibitory Effect on SLE-Like Disease Onset in Spontaneous Onset Model Using NZB/W F1 Mice NZB/W F1 mice (Japan SLC, Inc.) is used as a model of SLE spontaneously developing a disease condition close to humans ("JAMA", 1966, Vol. 195, p. 145; "Advances in Immunology", 1985, Vol. 37, p. 269-390; "Journal of Biomedicine and Biotechnology", 2011, Vol. 2011, 271694).

NZB/W F1 female mice were divided into groups according to urine protein values (creatinine corrected value), anti-double stranded DNA (dsDNA) antibody value (IgG) in plasma, an expression level of MHC class II in B cells of peripheral blood, and body weight at age of 19 weeks. At this time, individuals with urine protein values (creatinine corrected value) of 3 or more were excluded. From age of 20 weeks, the test compound was orally administered twice a day, and then urine collection and blood collection were performed over time. The change in urine protein value and anti-dsDNA antibody value over time were evaluated.

In the above test, anti-dsDNA IgG antibody value in plasma generated in association with SLE-like disease was measured by ELISA method (ALPHA DIAGNOSTIC 5120). In geometric mean values of the antibody value at age of 28 weeks and age of 32 weeks of each individual, a geometric mean value of 10 vehicle-administered subjects was 216662 U/mL, whereas a geometric mean value of 10 subjects administered with 1 mg/kg b.i.d. of the compound of Example 2 was 26827 U/mL, which is a low value having a significant difference (P value=0.0009, Dunnett's multiple comparison). In addition, urine protein values (creatinine corrected value) at age of 40 weeks were measured. A geometric mean value of the 10 vehicle-administered subjects was 13.0, whereas a geometric mean value of the 10 subjects administered with 1 mg/kg b.i.d. of the compound of Example 2 was 0.7, which is a low value having a significant difference (P value=0.0005, Dunnett's multiple comparison). Based on this, it was confirmed that the compound of Example 2 has the effect of suppressing the SLE-like disease onset in NZB/W F1 female mice.

Test Example 5: Evaluation of Therapeutic Effect on SLE-Like Disease in Poly (I:C) Induced Onset Model Using NZB/W F1 Mice The poly (I:C), which is a ligand for Toll-like receptor 3, is administered to NZB/W F1 mice (Japan SLC, Inc.), and therefore, it is possible to accelerate an increase in proteinuria associated with SLE-like disease. Administration of the test compound is started from the state where proteinuria is induced by poly (I:C) administration, and then a therapeutic effect of SLE-like disease is evaluated.

200 μg of poly (I:C) (InvivoGen tlrl-picw-250) is administered to 22-weeks-old NZB/W F1 mice three times a week for 4 weeks, which is a total of 12 times. In the following 2 weeks, individuals whose urine protein value (creatinine corrected value) has become 2 to 50 in principle are incorporated in the test and allocated based on the urine protein value. After grouping, the test compound is orally administered twice a day for 5 weeks, urine is collected over time, and therefore the change in urine protein value over time is evaluated.

Based on the above results, the compound of the formula (I) or a salt thereof is expected to be used as an agent for preventing and/or treating autoimmune disease including SLE and lupus nephritis, allergies, or graft rejection of an organ, bone marrow or tissue.

A pharmaceutical composition containing one or more compounds of the formula (I) or a salt thereof as an active ingredient can be prepared by using an excipient generally used in this field, that is, a pharmaceutical excipient, a pharmaceutical carrier, and the like, according to methods generally used.

Administration may be in any form of oral administration with tablets, pills, capsules, granules, powders, solutions, and the like, injections such as intra-articular, intravenous, and intramuscular injections, and parenteral administration by suppository, eye drops, eye ointment, transdermal solution, ointment, transdermal patch, transmucosal solution, transmucosal patch, inhaler, and the like.

As a solid composition for oral administration, tablets, powders, granules, and the like are used. In such solid compositions, one or more active ingredients are mixed with at least one inert excipient. The composition may contain inactive additives such as lubricants and disintegrants, stabilizers, and solubilizing agents according to general methods. The tablets or pills may be coated with a sugar coating or a film of stomach-soluble or enteric substance, if necessary.

Liquid compositions for oral administration include pharmaceutically acceptable emulsions, solutions, suspensions, syrups, elixirs, and the like, and include inert diluents generally used, such as purified water or ethanol. The liquid composition may contain a solubilizing agent, a wetting agent, an adjuvant such as a suspending agent, a sweetening agent, a flavor, an aromatic, and a preservative in addition to the inert diluent.

The injections for parenteral administration contain sterile aqueous or nonaqueous solutions, suspensions, or emulsions. Examples of the aqueous solvent include distilled water for injection or physiological saline. Examples of the nonaqueous solvents include alcohols such as ethanol. Such a composition may further include a tonicity agent, a preservative, a wetting agent, an emulsifying agent, a dispersing agent, a stabilizing agent, or a solubilizing agent. These are sterilized, for example, by filtration through a bacteria-retaining filter, and blending of a sterilizing agent or irradiation. These can also be used by preparing a sterile solid composition and dissolving or suspending the composition in sterile water or a sterile injectable solvent before use.

Examples of external preparations include ointments, plasters, creams, jellies, cataplasms, sprays, lotions, eye drops, eye ointments, and the like. Generally used ointment base, lotion base, aqueous or nonaqueous solutions, suspensions, emulsions, and the like are included therein.

Transmucosal agents such as inhalers and transnasal preparations are solid, liquid, or semisolid, and can be manufactured according to known methods of the related art. For example, well-known excipients, and furthermore, pH adjusters, preservatives, surfactants, lubricants, stabilizers, thickeners, and the like may be appropriately added. For administration, a device for proper inhalation or insufflation can be used. For example, using a known device such as metered-dose inhaler device, or a nebulizer, the compound can be administered alone or as a powder of the formulated mixture, or as a solution or suspension in combination with a pharmaceutically acceptable carrier. A dry powder inhaler and the like may be a device for single or multiple administrations, and a dry powder or a powder-containing capsule may be used. Alternatively, the administration form may be a suitable ejection agent such as a pressurized aerosol spray using a suitable gas such as chlorofluoroalkane or carbon dioxide.

In a case of the oral administration, a daily dose is about 0.001 to 100 mg/kg, preferably 0.1 to 30 mg/kg, and more preferably 0.1 to 10 mg/kg per body weight, which are suitable, and this dose is administered once or divided into 2 to 4 doses. In a case of intravenous administration, a daily dose is suitably about 0.0001 to 10 mg/kg per body weight, and this dose is administered once to several doses a day. In regard to a transmucosal agent, about 0.001 to 100 mg/kg per body weight is administered once to several doses a day. The dose is appropriately decided according to individual cases in consideration of symptoms, age, sex, and the like.

The pharmaceutical composition of the present invention contains 0.01% to 100% by weight, and 0.01% to 50% by weight in one embodiment, of one or more compounds of the formula (I) or a salt thereof, which is an active ingredient, although the weight thereof may vary depending on the route of administration, dosage form, site of administration, types of excipients and additives.

The compound of the formula (I) can be used in combination with various agents for treating or agents for preventing diseases on which the compound of the formula (I) is considered to exhibit efficacy. The combination may be administered simultaneously, or separately in succession, or at a desired time interval. An agent for simultaneous administration may be a compounding agent or may be separately formulated.

EXAMPLES

Hereinafter, a preparation method of the compound of the formula (I) will be explained in more detail based on examples. The present invention is not limited to compounds described in the following examples. In addition, each preparation method of a starting compound is shown in preparation examples. Furthermore, the preparation method of the compound of the formula (I) is not limited only to preparation methods of the specific examples shown below. The compound of the formula (I) can be prepared according to a combination of these preparation methods, or methods which are obvious for those skilled in the art.

An onset temperature of a DSC curve obtained by measurement under the following conditions is shown in the following tables as a melting point.

The DSC measurement was performed using an aluminum sample pan in a state of not covering the sample pan under conditions of a measurement range of temperature: room temperature to 300° C., an increase rate of temperature: 10° C./min, and a flow rate of nitrogen: 50 mL/min by using DSC Q2000 (manufactured by TA Instruments.).

Powder X-ray diffraction was performed by using RINT-TTR II (manufactured by RIGAKU Corporation) under conditions of a tube: Cu, a tube current: 300 mA, a tube voltage: 50 kV, a sampling width: 0.020°, a scanning speed: 4°/min, a wavelength: 1.5418 Å, a measured range of diffraction angle: (2θ): 2.5 to 40°.

In regard to a pattern of the powder X-ray diffraction, because of the nature of data thereof, crystal lattice space and overall patterns are important in identification of crystal identity an error range of a diffraction angle (2θ(°)) in the powder X-ray diffraction is generally ±0.2°, but a diffraction angle and a diffraction intensity can be changed depending on a direction of crystal growth, a size of the grains, and measuring conditions, and therefore the patterns should not be strictly interpreted.

The following abbreviations are sometimes used in the examples, preparation examples, and tables to be described later.

Pr=Preparation Example No., Ex=Example No., Syn=preparation method (indicating that preparation was performed in the same manner as in Example No. or Preparation Example No. described), Str=structural formula, Dat=physicochemical data, ESI+=m/z value of ESI-MS (representing [M+H]$^+$ unless specified otherwise), ESI-=m/z value of ESI-MS (representing [M−H]$^-$ unless specified otherwise), NMR1: δ (ppm) of peak in $^1$H NMR in DMSO-$d_6$ at room temperature, NMR2: δ (ppm) of peak in $^1$H NMR in DMSO-$d_6$ at 80° C., NMR3: δ (ppm) of peak in $^1$H NMR in DMSO-$d_6$ at 60° C., $[\alpha]_D^{23.5}$: D line, specific rotation at 23.5° C., m.p.: melting point, 2θ: diffraction angle of peak in powder X-ray diffraction.

HCl in a structural formula represents hydrochloride, and a number before HCl represents a molar ratio. For example, 2HCl means dihydrochloride. Similarly, SA represents succinate, and 2SA means disuccinate (including a co-crystal containing a compound and succinic acid in a molar ratio of 1:2).

The symbol gm noted in Preparation Example No. and Example No. represents a mixture of geometric isomers. Similarly, the symbol em represents a mixture of epimers at the 4-position of a pyrrolidine ring or a mixture of epimers at the 3-position of a pyrrolidine ring, and the symbol dm represents a mixture of diastereomers having different steric configurations at the α-position of a benzyl group and the 4-position of a pyrrolidine ring.

For convenience, a concentration mol/L is represented as M. For example, 1M of a sodium hydroxide aqueous solution means 1 mol/L of a sodium hydroxide aqueous solution.

Preparation Example 1

N-bromosuccinimide (148.9 g) and 47% hydrobromic acid (5 mL) were added to a MeCN (700 mL) solution of 4-bromo-1-methyl-2-(trifluoromethyl) benzene (100 g) at room temperature under an argon gas atmosphere. To the mixture, 2,2'-azobis(isobutyronitrile) (3.43 g) was added, stirred at 70° C. for 10 minutes, and then stirred at 100° C. overnight. The mixture was cooled to room temperature. The mixture was ice-cooled, a saturated aqueous sodium thiosulfate solution was added, and the mixture was stirred for 10 minutes. Water and EtOAc were added to the mixture. The organic layer was separated and washed with a saturated aqueous sodium bicarbonate solution and brine. The organic layer was dried over anhydrous sodium sulfate and concentrated under reduced pressure. To the residue, n-hexane was added, and the precipitated solid was separated by filtration. The filtrate was concentrated under reduced pressure. DIPEA (79 mL) and diethyl phosphonate (54 mL) were added to a THF (500 mL) solution of the residue while ice cooling. The mixture was stirred at room temperature for 2 hours. The mixture was ice-cooled and water was added thereto. To the mixture, EtOAc was added, and the organic layer was separated and washed with hydrochloric acid (1 M), water, a saturated aqueous sodium bicarbonate solution and brine. The organic layer was dried over MgSO$_4$ and concentrated under reduced pressure. Triphenylphosphine (115 g) was added to a toluene (700 mL) solution of the residue, and the mixture was stirred overnight at 100° C. The precipitate was collected by filtration and washed with toluene to obtain [4-bromo-2-(trifluoromethyl)benzyl](triphenyl)phosphonium bromide (198.51 g) as a solid.

Preparation Example 2

Potassium tert-butoxide (27.5 g) was added to a dichloromethane (600 mL) solution of [4-bromo-2-(trifluoromethyl)benzyl](triphenyl)phosphonium bromide (150 g) under an argon gas atmosphere while ice cooling, and the mixture was stirred at room temperature for 6 hours. The mixture was ice-cooled and a dichloromethane (150 mL) solution of (2S)-4-oxopyrrolidine-1,2-dicarboxylic acid 1-tert-butyl ester 2-methyl ester (50 g) was added thereto, and the mixture was stirred at room temperature for 4 days. A saturated aqueous ammonium chloride solution was added to the mixture and stirred for 15 minutes. The organic layer was separated, and the aqueous layer was extracted with chloroform. The combined organic layers were washed with brine. The organic layer was dried over MgSO$_4$ and concentrated under reduced pressure. EtOAc (40 mL) and n-hexane (200 mL) were added to the residue, and the mixture was stirred at room temperature for 1 hour. The precipitate was separated by filtration, and the filtrate was concentrated under reduced pressure. The residue was purified by silica gel column chromatography (eluent; n-hexane/EtOAc) to obtain (2S)-4-[4-bromo-2-(trifluoromethyl)benzylidene]pyrrolidine-1,2-dicarboxylic acid 1-tert-butyl ester 2-methyl ester (mixture of geometric isomers) (51.74 g) as an oily substance.

Preparation Example 3

Borane-THF complex (1 M THF solution, 167 mL) was added to a THF (100 mL) solution of (2S)-4-[4-bromo-2-(trifluoromethyl)benzylidene]pyrrolidine-1,2-dicarboxylic acid 1-tert-butyl ester 2-methyl ester (mixture of geometric isomers) (25.9 g) under an argon gas atmosphere while ice cooling. The mixture was stirred at 30° C. for 30 minutes. The mixture was cooled using an ice water bath to which sodium chloride was added, and MeOH (27 mL) was added thereto. To the mixture, a mixture of an NaOH aqueous solution (1 M, 112 mL) and a 30% hydrogen peroxide aqueous solution (18 mL) was added, and the mixture was stirred at room temperature for 1 hour. The mixture was ice-cooled and EtOAc and a 14% sodium thiosulfate aqueous solution were added. The mixture was stirred at room temperature for 1 hour. The organic layer was separated and washed with brine. The organic layer was dried over MgSO$_4$ and concentrated under reduced pressure. The residue was purified by silica gel column chromatography (eluent; n-hexane/EtOAc) to obtain (2S)-4-{[4-bromo-2-(trifluoromethyl)phenyl](hydroxy)methyl}pyrrolidine-1,2-dicarboxylic acid 1-tert-butyl ester 2-methyl ester (a mixture of diastereomers having different steric configurations at the α-position of a benzyl group and the 4-position of a pyrrolidine ring) (20.96 g) as a solid.

Preparation Example 4

4-methylmorpholine N-oxide (6.1 g) and molecular sieve 4A (8.7 g) were added to a dichloromethane (105 mL) solution of (2S)-4-{[4-bromo-2-(trifluoromethyl)phenyl](hydroxy)methyl}pyrrolidine-1,2-dicarboxylic acid 1-tert-butyl ester 2-methyl ester (a mixture of diastereomers having different steric configurations at the α-position of a benzyl group and the 4-position of a pyrrolidine ring) (20.96 g) under a nitrogen gas atmosphere while ice cooling, and the mixture was stirred for 10 minutes. Tetrapropylammonium perruthenate (1.5 g) was added to the mixture while ice cooling, and the mixture was stirred at room temperature for 1 hour. EtOAc was added to the mixture and concentrated under reduced pressure. The residue was filtered using silica gel and washed with EtOAc. A saturated sodium thiosulfate aqueous solution was added to the filtrate, and the mixture was stirred. The organic layer was separated and washed with brine. The organic layer was dried over MgSO$_4$ and concentrated under reduced pressure. The residue was purified by silica gel column chromatography (eluent; n-hexane/EtOAc) to obtain (2S)-4-[4-bromo-2-(trifluoromethyl)benzoyl]pyrrolidine-1,2-dicarboxylic acid 1-tert-butyl ester 2-methyl ester (a mixture of epimers at the 4-position of a pyrrolidine ring) (19.6 g) as an oily substance.

Preparation Example 5

Hydrogen chloride (4 M 1,4-dioxane solution, 395 mL) was added to a MeOH (395 mL) suspension of (2S)-4-[4-bromo-2-(trifluoromethyl)benzoyl]pyrrolidine-1,2-dicarboxylic acid 1-tert-butyl ester 2-methyl ester (a mixture of epimers at the 4-position of a pyrrolidine ring) (78.9 g) while ice cooling, and the mixture was stirred at room temperature for 1 hour. The mixture was concentrated under reduced pressure. Toluene was added to the mixture, and the mixture was concentrated under reduced pressure. 1-Methylcyclopropanecarboxylic acid (20 g), HATU (76 g), and DIPEA (86 mL) were added to a dichloromethane (630 mL) solution of the residue under a nitrogen gas atmosphere while ice cooling, and the mixture was stirred for 5 hours at room temperature. The mixture was ice-cooled, and a saturated aqueous sodium bicarbonate solution was added thereto. Chloroform was added to the mixture, and the organic layer was separated and washed with hydrochloric acid (1 M), a saturated aqueous sodium bicarbonate solution, and brine. The organic layer was dried over anhydrous sodium sulfate and concentrated under reduced pressure. The residue was purified by amino silica gel column chromatography (eluent; n-hexane/EtOAc) and silica gel column chromatography (eluent; n-hexane/EtOAc) to obtain 4-[4-bromo-2-(trifluoromethyl)benzoyl]-1-[(1-methylcyclopropyl)carbonyl]-L- proline methyl ester (a mixture of epimers at the 4-position of a pyrrolidine ring) (57.65 g) as an oily substance.

Preparation Example 6

Using a reaction vessel made of Teflon (registered trademark), 4-tert-butyl-2,6-dimethylphenylsulfur trifluoride (138.6 g) and hydrogen fluoride pyridine (101.5 mL) were added to a dichloromethane (320 mL) solution of 4-[4-bromo-2-(trifluoromethyl)benzoyl]-1-[(1-methylcyclopropyl)carbonyl]-L-proline methyl ester (a mixture of epimers at the 4-position of a pyrrolidine ring) (64 g) under an argon gas atmosphere, and the mixture was stirred for 15 hours at room temperature. Stirring of the reaction vessel was stopped, and the mixture was left to stand at room temperature for 75 hours. The mixture was added to a mixture of ice and 28% aqueous ammonia solution (1400 mL). Chloroform was added to the mixture, and the mixture was stirred for 8 hours. The organic layer was separated, and the aqueous layer was extracted with chloroform. The combined organic layers were washed with a saturated aqueous sodium bicarbonate solution, hydrochloric acid (1 M), a saturated aqueous sodium bicarbonate solution, and brine. The organic layer was dried over $MgSO_4$ and concentrated under reduced pressure. To the residue, n-hexane was added, and the mixture was stirred at room temperature for 1 hour. The insoluble material was separated by filtration, and the filtrate was concentrated under reduced pressure. The residue was purified by silica gel column chromatography (eluent; n-hexane/EtOAc). The obtained oily substance was mixed with n-hexane (253 mL) and EtOAc (2.5 mL). The mixture was heated, and when the solid was precipitated, the mixture was allowed to cool and was stirred for 15 hours at room temperature. The precipitate was collected by filtration and washed with a mixture of n-hexane and EtOAc (99:1) to obtain (4R)-4-{[4-bromo-2-(trifluoromethyl)phenyl](difluoro)methyl}-1-[(1-methylcyclopropyl)carbonyl]-L-proline methyl ester (26.6 g) as a solid.

Preparation Example 7

An aqueous solution of lithium hydroxide hydrate (1 M, 82 mL) was added to a mixture of (4R)-4-{[4-bromo-2-(trifluoromethyl)phenyl](difluoro)methyl}-1-[(1-methylcyclopropyl)carbonyl]-L-proline methyl ester (26.57 g) and THF (265 mL) while ice cooling, and the mixture was stirred at room temperature for 2 hours. The mixture was ice-cooled, and hydrochloric acid (1 M, about 85 mL) was added thereto. EtOAc was added to the mixture, and the organic layer was separated and washed with brine. The organic layer was dried over anhydrous sodium sulfate and concentrated under reduced pressure to obtain (4R)-4-{[4-bromo-2-(trifluoromethyl)phenyl](difluoro)methyl}-1-[(1-methylcyclopropyl)carbonyl]-L-proline (26.03 g) as a solid.

Preparation Example 8

1-Aminocyclopropanecarbonitrile hydrochloride (7.19 g), HATU (21.9 g), and DIPEA (23.5 mL) were added to a dichloromethane (258 mL) solution of (4R)-4-{[4-bromo-2-(trifluoromethyl)phenyl](difluoro)methyl}-1-[(1-methylcyclopropyl)carbonyl]-L-proline (25.80 g) while ice-cooling. The mixture was stirred at room temperature for 15 hours. Chloroform and a saturated aqueous ammonium chloride solution were added to the mixture. The organic layer was separated and washed with a saturated aqueous sodium bicarbonate solution and brine. The organic layer was dried over anhydrous sodium sulfate and concentrated under reduced pressure. The residue was purified by silica gel column chromatography (eluent; n-hexane/EtOAc) to obtain (4R)-4-{[4-bromo-2-(trifluoromethyl)phenyl](difluoro)methyl}-N-(1-cyanocyclopropyl)-1-[(1-methylcyclopropyl)carbonyl]-L-prolinamide (28.68 g) as a solid.

Preparation Example 9

Using a reaction vessel made of Teflon (registered trademark), 4-tert-butyl-2,6-dimethylphenylsulfur trifluoride (25 g) and hydrogen fluoride pyridine (18 mL) were added to a dichloromethane (64 mL) solution of 4-[4-bromo-2-(trifluoromethyl)benzoyl]-1-{[1-(trifluoromethyl)cyclopropyl]carbonyl}-L-proline methyl ester (a mixture of epimers at the 4-position of a pyrrolidine ring) (12.9 g) under an argon gas atmosphere, and the mixture was stirred for 9 hours at room temperature. Stirring of the reaction vessel was stopped, and the mixture was left to stand at room temperature for 14 hours. The mixture was stirred at room temperature for 11 hours. Stirring of the reaction vessel was stopped, and the mixture was left to stand at room temperature for 14 hours. The mixture was added to a mixture of ice, 28% aqueous ammonia solution (220 mL), and chloroform, and stirred for 3 hours. The organic layer was separated, and the aqueous layer was extracted with chloroform. The combined organic layers were dried over anhydrous sodium sulfate and concentrated under reduced pressure. To the residue, n-hexane was added, and the mixture was stirred at room temperature for 1 hour. The insoluble material was separated by filtration, and the filtrate was concentrated under reduced pressure. Toluene was added to the residue and concentrated under reduced pressure. The residue was purified by silica gel column chromatography (eluent; n-hexane/EtOAc) to obtain 4-{[4-bromo-2-(trifluoromethyl)phenyl](difluoro)methyl}-1-{[1-(trifluoromethyl)cyclopropyl]carbonyl}-L-proline methyl ester (a mixture of epimers at the 4-position of a pyrrolidine ring) (11.67 g) as an oily substance.

Preparation Example 10

4-{[4-Bromo-2-(trifluoromethyl)phenyl](difluoro)methyl}-1-{[1-(trifluoromethyl)cyclopropyl]carbonyl}-L-proline methyl ester (a mixture of epimers at the 4-position of a pyrrolidine ring) (3.69 g) was purified by column chromatography (column: CHIRALPAK IA, eluent: n-hexane/EtOAc) to obtain (4R)-4-{[4-bromo-2-(trifluoromethyl)phenyl](difluoro)methyl}-1-{[1-(trifluoromethyl)cyclopropyl]carbonyl}-L-proline methyl ester (1.91 g) as an oily substance.

Preparation Example 11

A mixture of 1,4-dioxane (10 mL) of 4-{[4-bromo-2-(trifluoromethyl)phenyl](difluoro)methyl}-1-[(1-methylcyclopropyl)carbonyl]-L-proline methyl ester (a mixture of epimers at the 4-position of a pyrrolidine ring) (478 mg), potassium trifluoro[(4-methylpiperazin-1-yl)methyl]borate (1-) (435 mg), palladium(II) acetate (23 mg), RuPhos (97 mg), and $K_3PO_4$ (839 mg), and water (0.072 mL) was stirred overnight at 80° C. under an argon gas atmosphere. A saturated aqueous sodium bicarbonate solution was added to the mixture. Chloroform was added to the mixture, and the organic layer was separated. The organic layer was washed with brine and concentrated under reduced pressure. The residue was purified by amino silica gel column chromatography (eluent; chloroform/MeOH) to obtain 4-(difluoro {4-[(4-methylpiperazin-1-yl)methyl]-2-(trifluoromethyl) phenyl}methyl)-1-[(1-methylcyclopropyl)carbonyl]-L-proline methyl ester (a mixture of epimers at the 4-position of a pyrrolidine ring) (340 mg) as an oily substance.

Preparation Example 12

Triphenylphosphine (9.75 g) was added to a toluene (70 mL) solution of 4-bromo-1-(bromomethyl)-2-chlorobenzene (10 g) at room temperature, and the mixture was stirred at 80° C. for 6 hours. The mixture was ice-cooled and stirred for 30 minutes. The precipitate was collected by filtration and washed with toluene to obtain (4-bromo-2-chlorobenzyl)(triphenyl)phosphonium bromide (18.9 g) as a solid.

Preparation Example 13

2,4,6-Trichlorophenyl formate (1 g), palladium(II) acetate (120 mg), XantPhos (300 mg), and DIPEA (1.5 mL) were added to a toluene (30 mL) solution of 4-{[4-bromo-2-(trifluoromethyl)phenyl](difluoro)methyl}-N-(1-cyanocyclopropyl)-1-{[1-(trifluoromethyl)cyclopropyl]carbonyl}-L-prolinamide (a mixture of epimers at the 4-position of a pyrrolidine ring) (2.1 g) at 100° C. under an argon gas atmosphere, and the mixture was stirred for 1 hour. The mixture was ice-cooled, and chloroform and brine were added thereto. The insoluble material was separated by filtration with Celite, and the organic layer of the filtrate was separated. The organic layer was dried over anhydrous sodium sulfate and concentrated under reduced pressure. The residue was purified by silica gel column chromatography (eluent: n-hexane/EtOAc) to obtain 4-{[(5S)-5-[1-cyanocyclopropyl)carbomoyl]-1-{[1-(trifluoromethyl)cyclopropyl]carbonyl}pyrrolidin-3-yl](difluoro)methyl}-3-(trifluoromethyl)benzoic acid 2,4,6-trichlorophenyl ester (a mixture of epimers at the 3-position of a pyrrolidine ring) (2.4 g) as a solid.

Preparation Example 14

Sodium borohydride (103 mg) was added to a mixture of 4-{[(5S)-5-[(1-cyanocyclopropyl)carbamoyl]-1-{[1-(trifluoromethyl)cyclopropyl]carbonyl}pyrrolidin-3-yl](difluoro)methyl}-3-(trifluoromethyl)benzoic acid 2,4,6-trichlorophenyl ester (a mixture of epimers at the 3-position of a pyrrolidine ring) (1 g) and THF (20 mL) while ice cooling. MeOH (2 mL) was added to the mixture while ice cooling, and the mixture was stirred at room temperature for 30 minutes. Water was added to the mixture. EtOAc was added to the mixture, and the organic layer was separated and washed with brine. The organic layer was dried over MgSO₄ and concentrated under reduced pressure. The residue was purified by silica gel column chromatography (eluent; n-hexane/EtOAc) to obtain N-(1-cyanocyclopropyl)-4-{difluoro[4-(hydroxymethyl)-2-(trifluoromethyl) phenyl]methyl}-1-{[1-(trifluoromethyl)cyclopropyl]carbonyl}-L-prolinamide (a mixture of epimers at the 4-position of a pyrrolidine ring) (290 mg) as a solid.

Preparation Example 15

A mixture of 1,2-dibromoethane (0.032 mL) and chloro (trimethyl)silane (0.047 mL) was added to a suspension of zinc (365 mg) in N,N-dimethylacetamide (2 mL) at room temperature under an argon gas atmosphere, and the mixture was stirred at 50° C. for 15 minutes. To the mixture, a N,N-dimethylacetamide (2 mL) solution of 4-iodopiperidine-1-carboxylic acid tert-butyl ester (1.73 g) was added at room temperature, and the mixture was stirred at 50° C. for 15 minutes. The above mixture was added to a N,N-dimethylacetamide (5 mL) suspension of 4-{[4-bromo-2-(trifluoromethyl)phenyl](difluoro)methyl}-1-{[1-(trifluoromethyl)cyclopropyl]carbonyl}-L-proline methyl ester (a mixture of epimers at the 4-position of a pyrrolidine ring) (1 g), 1,1'-bis(diphenylphosphino)ferrocene-palladium(II) dichloride-dichloromethane complex (151 mg), and copper iodide (I) (71 mg) at room temperature under an argon gas atmosphere, and the mixture was stirred at 80° C. overnight. The mixture was cooled to room temperature, EtOAc was added, and the insoluble material was separated by filtration. The filtrate was washed with water and brine, and the organic layer was dried over MgSO₄ and concentrated under reduced pressure. The residue was purified by silica gel column chromatography (eluent: n-hexane/EtOAc) to obtain 4-[4-{difluoro[(5S)-5-(methoxycarbonyl)-1-{[1-(trifluoromethyl)cyclopropyl]carbonyl}pyrrolidin-3-yl]methyl}-3-(trifluoromethyl)phenyl]piperidine-1-carboxylic acid tert-butyl ester (a mixture of epimers at the 3-position of a pyrrolidine ring) (1.15 g) as an oily substance.

Preparation Example 16

Trifluoroacetic acid (1.5 mL) was added to a dichloromethane (15 mL) and MeCN (7.5 mL) solution of 4-[4-{[(5S)-5-[(1-cyanocyclopropyl)carbamoyl]-1-{[1-(trifluoromethyl)cyclopropyl]carbonyl}pyrrolidin-3-yl](difluoro) methyl}-3-(trifluoromethyl)phenyl]piperidine-1-carboxylic acid tert-butyl ester (a mixture of epimers at the 3-position of a pyrrolidine ring) (675 mg) while ice cooling, and the mixture was stirred at room temperature for 3 hours. Trifluoroacetic acid (2.25 mL) was added to the mixture at room temperature, and the mixture was stirred for 4 hours. The mixture was added to a saturated aqueous sodium bicarbonate solution. Chloroform was added to the mixture, and the organic layer was separated and washed with brine. The organic layer was dried over MgSO₄ and concentrated under reduced pressure to obtain N-(1-cyanocyclopropyl)-4-{difluoro[4-(piperidin-4-yl)-2-(trifluoromethyl)phenyl] methyl}-1-{[1-(trifluoromethyl)cyclopropyl]carbonyl}-L-prolinamide (a mixture of epimers at the 4-position of a pyrrolidine ring) (509 mg) as a solid.

Preparation Example 17

Potassium carbonate (5.5 g) was added to a dichloromethane (80 mL) solution of (4-bromo-2-chlorobenzyl) (triphenyl)phosphonium bromide (18.9 g) at room temperature under a nitrogen gas atmosphere, and the mixture was stirred for 20 minutes. To the mixture, (2S)-4-oxopyrrolidine-1,2-dicarboxylic acid 1-tert-butyl ester 2-methyl ester (6.5 g) and 18-crown-6 (110 mg) were added at room temperature, and the mixture was stirred while heating under reflux for 3 days. The mixture was ice-cooled, and a saturated aqueous sodium bicarbonate solution was added thereto. The organic layer was separated and washed with brine. The organic layer was dried over anhydrous sodium sulfate and concentrated under reduced pressure. The residue was purified by silica gel column chromatography (eluent; n-hexane/EtOAc) to obtain (2S)-4-(4-bromo-2-chlorobenzylidene)pyrrolidine-1,2-dicarboxylic acid 1-tert-butyl ester 2-methyl ester (a mixture of geometric isomers) (5.17 g) as an oily substance.

Preparation Example 18

Bis(2-methoxyethyl)aminosulfur trifluoride (15 mL) was added to 4-(4-bromo-2-chlorobenzoyl)-1-{[1-(trifluoromethyl)cyclopropyl]carbonyl}-L-proline methyl ester (a mixture of epimers at the 4-position of a pyrrolidine ring) (2.8 g) under an argon gas atmosphere, and the mixture was stirred at 90° C. for 3 hours. The mixture was ice-cooled and added to a mixture of ice and saturated aqueous sodium bicarbonate solution. EtOAc was added to the mixture, and the organic layer was separated and washed with brine. The organic layer was dried over anhydrous sodium sulfate and concentrated under reduced pressure. The residue was purified by silica gel column chromatography (eluent; n-hexane/ EtOAc) to obtain 4-[(4-bromo-2-chlorophenyl)(difluoro) methyl]-1-{[1-(trifluoromethyl)cyclopropyl]carbonyl}-L-proline methyl ester (mixture of epimers at the 4-position of a pyrrolidine ring) (2.37 g) as an oily substance.

Preparation Example 19

Lithium hydroxide hydrate (20 mg) was added to a MeOH (0.7 mL) and THF (0.7 mL) solution of 4-(4-{difluoro[(5S)-5-(methoxycarbonyl)-1-{[1-(trifluoromethyl)cyclopropyl] carbonyl}pyrrolidin-3-yl]methyl}-3-fluorophenyl)piperidine-1-carboxylic acid tert-butyl ester (a mixture of epimers at the 3-position of a pyrrolidine ring) (105 mg) at room temperature, and the mixture was stirred at room temperature for 1 hour. The mixture was concentrated under reduced pressure to obtain lithium (2S)-4-[{4-[1-(tert-butoxycarbonyl)piperidin-4-yl]-2-fluorophenyl}(difluoro)methyl]-1-{[1-(trifluoromethyl)cyclopropyl]carbonyl}pyrrolidine-2-carboxylate (a mixture of epimers at the 4-position of a pyrrolidine ring) (102 mg) as a solid.

Example 1

Potassium trifluoro[(4-methylpiperazin-1-yl)methyl] borate(1-) (4.1 g), XPhos (892 mg), cesium carbonate (12 g), and palladium acetate (II) (214 mg) were added to a 1,4-dioxane (50 mL) and water (10 mL) solution of (4R)-4-{ [4-bromo-2-(trifluoromethyl)phenyl](difluoro)methyl}-N-(1-cyanocyclopropyl)-1-[(1-methylcyclopropyl)carbonyl]-L-prolinamide (5 g) at room temperature under an argon gas atmosphere, and the mixture was stirred for 3 hours while heating under reflux. The mixture was cooled to room temperature and water was added thereto. The insoluble material was separated by filtration with Celite and washed with chloroform. Water and chloroform were added to the filtrate. The organic layer was separated and washed with brine. The organic layer was dried over MgSO$_4$ and concentrated under reduced pressure. The residue was purified by silica gel column chromatography (eluent; n-hexane/ EtOAc and chloroform/MeOH) to obtain (4R)—N-(1-cyanocyclopropyl)-4-(difluoro{4-[(4-methylpiperazin-1-yl) methyl]-2-(trifluoromethyl)phenyl}methyl)-1-[(1-methylcyclopropyl)carbonyl]-L-prolinamide (4.7 g) as a solid.

Example 2

Hydrogen chloride (4 M 1,4-dioxane solution, 1.39 mL) was added to an EtOAc (7 mL) and ethanol (7 mL) solution of (4R)—N-(1-cyanocyclopropyl)-4-(difluoro{4-[(4-methylpiperazin-1-yl)methyl]-2-(trifluoromethyl) phenyl}methyl)-1-[(1-methylcyclopropyl)carbonyl]-L-prolinamide (1.43 g), and the mixture was stirred at room temperature for 30 minutes. The mixture was concentrated under reduced pressure. Ethanol was added to the residue, and the mixture was concentrated under reduced pressure. EtOAc was added to the residue, and the mixture was stirred for about 1 hour. The mixture was concentrated under reduced pressure. Ethanol (10 mL) was added to the residue and heated at 95° C. to obtain a solution. The mixture was stirred overnight at room temperature. The precipitate was collected by filtration and washed with ethanol to obtain (4R)—N-(1-cyanocyclopropyl)-4-(difluoro {4-[(4-methylpiperazin-1-yl)methyl]-2-(trifluoromethyl)phenyl}methyl)-1-[(1-methylcyclopropyl)carbonyl]-L-prolinamide dihydrochloride (516 mg) as a solid.

Example 4

A mixture of (4R)-4-{[4-bromo-2-(trifluoromethyl)phenyl](difluoro)methyl}-N-(1-cyanocyclopropyl)-1-{[1-(trifluoromethyl)cyclopropyl]carbonyl}-L-prolinamide (627.4 mg), potassium trifluoro[(4-methylpiperazin-1-yl)methyl] borate(1-) (705 mg), palladium(II) acetate (25 mg), RuPhos (105 mg), K$_3$PO$_4$ (905 mg), 1,4-dioxane (13 mL), and water (1.3 mL) was stirred at 80° C. for 6 hours under an argon gas atmosphere. A saturated aqueous sodium bicarbonate solution and chloroform were added to the mixture. The organic layer was separated and washed with brine. The organic layer was dried over MgSO$_4$ and concentrated under reduced pressure. The residue was purified by amino silica gel column chromatography (eluent; chloroform/MeOH) to obtain (4R)—N-(1-cyanocyclopropyl)-4-(difluoro{4-[(4-methylpiperazin-1-yl)methyl]-2-(trifluoromethyl) phenyl}methyl)-1-{[1-(trifluoromethyl)cyclopropyl]carbonyl}-L-prolinamide (491.4 mg) as an oily substance.

Example 7

Hydrochloric acid (6 M, 0.678 mL) was added to an ethanol (6 mL) solution of 4-{4-[{(3R,5S)-5-[(1-cyanocyclopropyl)carbamoyl]-1-[(1-methylcyclopropyl)carbonyl] pyrrolidin-3-yl}(difluoro)methyl]-3-(trifluoromethyl) benzyl}piperazine-1-carboxylic acid tert-butyl ester (339 mg), and stirred at 50° C. for 1 hour. The mixture was stirred at 60° C. for 5 hours. The mixture was ice-cooled, and aqueous NaOH solution (1 M, 5 mL) was added thereto. Chloroform was added to the mixture, and the organic layer was separated and concentrated under reduced pressure. The residue was purified by amino silica gel column chromatography (eluent; chloroform/MeOH). Hydrogen chloride (4 M 1,4-dioxane solution, 0.285 mL) was added to a solution of 1,4-dioxane (3 mL) and ethanol (5 mL) of the obtained oily substance, and the mixture was stirred at room temperature for 5 minutes. The mixture was concentrated under reduced pressure. EtOAc was added to the residue, and the precipitate was collected by filtration and washed with EtOAc to obtain (4R)—N-(1-cyanocyclopropyl)-4-{difluoro[4-(piperazin-1-ylmethyl)-2-(trifluoromethyl)phenyl] methyl}-1-[(1-methylcyclopropyl)carbonyl]-L-prolinamide dihydrochloride (190 mg) as a solid.

Example 8

A mixture of 4-(difluoro{4-[(4-methylpiperazin-1-yl) methyl]-2-(trifluoromethyl)phenyl}methyl)-1-[(1-methylcyclopropyl)carbonyl]-L-proline (a mixture of epimers at the 4-position of a pyrrolidine ring) (415 mg), 1-aminocyclopropanecarbonitrile hydrochloride (117 mg), HATU (375 mg), DIPEA (0.338 mL), and DMF (8 mL) was stirred overnight at room temperature. Water was added to the mixture, and the mixture was extracted with chloroform. The organic layer was concentrated under reduced pressure. The residue was purified by amino silica gel column chromatography (eluent; chloroform/MeOH). The obtained oily substance was purified by reversed-phase high-performance liquid chromatography (eluent; 0.1% formic acid aqueous solution/MeCN). Hydrogen chloride (4 M 1,4-dioxane solution, 0.115 mL) was added to a dichloromethane (1 mL) solution of the obtained residue, and the mixture was stirred at room temperature for 5 minutes. The mixture was concentrated under reduced pressure to obtain N-(1-cyanocyclopropyl)-4-(difluoro{4-[(4-methylpiperazin-1-yl)methyl]-2-(trifluoromethyl)phenyl}methyl)-1-[(1-methylcyclopropyl)carbonyl]-L-prolinamide dihydrochloride (a mixture of epimers at the 4-position of a pyrrolidine ring) (62 mg) as a solid.

Example 9

Trifluoroacetic acid (0.11 mL) was added to a dichloromethane (0.42 mL) and MeCN (0.11 mL) solution of 4-[4-{[(3R,5S)-5-[(1-cyanocyclopropyl)carbamoyl]-1-{[1-(trifluoromethyl)cyclopropyl]carbonyl}pyrrolidin-3-yl](difluoro)methyl}-3-(trifluoromethyl)benzyl]piperazine-1-carboxylic acid tert-butyl ester (35 mg) while ice cooling, and the mixture was stirred overnight at room temperature. The mixture was concentrated under reduced pressure. The residue was purified by amino silica gel column chromatography (eluent; chloroform/MeOH). Hydrogen chloride (4 M 1,4-dioxane solution, 0.015 mL) was added to a 1,4-dioxane (0.35 mL) solution of the obtained residue, and the mixture was stirred at room temperature for 5 minutes. The mixture was concentrated under reduced pressure, and diisopropyl ether was added to the residue. The precipitate was collected by filtration to obtain (4R)—N-(1-cyanocyclopropyl)-4-{difluoro[4-(piperazin-1-ylmethyl)-2-(trifluoromethyl)phenyl]methyl}-1-{[1-(trifluoromethyl)cyclopropyl]carbonyl}-L-prolinamide dihydrochloride (22 mg) as a solid.

Example 10

Methanesulfonyl chloride (0.011 mL) and TEA (0.039 mL) were added to a dichloromethane (2 mL) solution of N-(1-cyanocyclopropyl)-4-{difluoro[4-(hydroxymethyl)-2-(trifluromethyl)phenyl]methyl}-1-{[1-(trifluoromethyl)cyclopropyl]carbonyl}-L-prolinamide (a mixture of epimers at the 4-position of a pyrrolidine ring) (50 mg), and the mixture was stirred at room temperature for 30 minutes. The mixture was concentrated under reduced pressure. DMF (2 mL), 1-ethylpiperazine (0.024 mL), and potassium carbonate (86 mg) were added to the residue, and the mixture was stirred at room temperature for 20 hours. Water and EtOAc were added to the mixture, and the organic layer was separated and washed with water and brine. The organic layer was dried over anhydrous sodium sulfate and concentrated under reduced pressure. The residue was purified by amino silica gel column chromatography (eluent: n-hexane/chloroform, and chloroform/MeOH) to obtain N-(1-cyanocyclopropyl)-4-[{4-[(4-ethylpiperazin-1-yl)methyl]-2-(trifluoromethyl)phenyl}(difluoro)methyl]-1-{[1-(trifluoromethyl)cyclopropyl]carbonyl}-L-prolinamide (a mixture of epimers at the 4-position of a pyrrolidine ring) (52 mg) as a solid.

Example 12

Hydrogen chloride (4 M EtOAc solution, 0.455 mL) was added to an EtOAc (12 mL) and ethanol (1.2 mL) solution of (4R)—N-(1-cyanocyclopropyl)-4-(difluoro{4-[(4-methylpiperazin-1-yl)methyl]-2-(trifluoromethyl)phenyl}methyl-1-{[1-(trifluoromethyl)cyclopropyl]carbonyl}-L-prolinamide (565.9 mg), and the mixture was stirred at room temperature overnight. The precipitate was collected by filtration and washed with EtOAc to obtain (4R)—N-(1-cyanocyclopropyl)-4-(difluoro{4-[(4-methylpiperazin-1-yl)methyl]-2-(trifluoromethyl)phenyl}methyl)-1-{[1-(trifluoromethyl)cyclopropyl]carbonyl}-L-prolinamide dihydrochloride (508 mg) as a solid.

Example 15

Acetic acid (0.010 mL) and sodium triacetoxyborohydride (50 mg) were added to a dichloroethane (1 mL) solution of N-(1-cyanocyclopropyl)-4-{difluoro[2-fluoro-4-(piperidin-4-yl)phenyl]methyl}-1-{[1-(trifluoromethyl)cyclopropyl]carbonyl}-L-prolinamide (a mixture of epimers at the 4-position of a pyrrolidine ring) (32 mg) under an argon gas atmosphere while ice cooling, and the mixture was stirred for several minutes. Acetaldehyde (0.030 mL) was added to the mixture while ice cooling, and the mixture was stirred for 30 minutes. A saturated aqueous sodium bicarbonate solution was added to the mixture while ice cooling, and the organic layer was separated and washed with brine. The organic layer was dried over anhydrous sodium sulfate and concentrated under reduced pressure. The residue was purified by amino silica gel column chromatography (eluent; n-hexane/EtOAc) to obtain N-(1-cyanocyclopropyl)-4-{[4-(1-ethylpiperidin-4-yl)-2-fluorophenyl](difluoro)methyl}-1-{[1-(trifluoromethyl)cyclopropyl]carbonyl}-L-prolinamide (a mixture of epimers at the 4-position of a pyrrolidine ring) (27 mg) as a solid.

Example 17

Acetic acid (0.019 mL) and acetaldehyde (0.045 mL) were added to a dichloroethane (1.9 mL) solution of N-(1-cyanocyclopropyl)-4-{difluoro[4-(piperidin-4-yl)-2-(trifluoromethyl)phenyl]methyl}-1-{[1-(trifluoromethyl)cyclopropyl]carbonyl}-L-prolinamide (a mixture of epimers at the 4-position of a pyrrolidine ring) (95 mg) at room temperature, and the mixture was stirred for 5 minutes. Sodium triacetoxyborohydride (136 mg) was added to the mixture at room temperature, and the mixture was stirred for 2 hours. Water and chloroform were added to the mixture, and the organic layer was separated and washed with brine. The organic layer was dried over MgSO$_4$ and concentrated under reduced pressure. The residue was purified by silica gel column chromatography (eluent; chloroform/MeOH). Hydrogen chloride (4 M 1,4-dioxane solution, 0.025 mL) was added to a dichloromethane (2 mL) solution of the obtained oily substance, and the mixture was stirred for 30 minutes. The mixture was concentrated under reduced pressure to obtain N-(1-cyanocyclopropyl)-4-{[4-(1-ethylpiperidin-4-yl)-2-(trifluoromethyl)phenyl](difluoro)methyl}-1-{[1-(trifluoromethyl)cyclopropyl]carbonyl}-L-prolinamide hydrochloride (a mixture of epimers at the 4-position of a pyrrolidine ring) (60.6 mg) as a solid.

Example 18

Succinic acid (104 mg) was added to a 2-propanol (2.5 mL) solution of (4R)—N-(1-cyanocyclopropyl)-4-(difluoro{4-[(4-methylpiperazin-1-yl)methyl]-2-(trifluoromethyl)phenyl}methyl)-1-[(1-methylcyclopropyl)carbonyl]-L-prolinamide (250 mg) at room temperature. The mixture was stirred at 60° C. for 5 minutes and then stirred at room temperature overnight. 2-Propanol (2.5 mL) was added to the mixture and stirred for 10 minutes. The precipitate was collected by filtration and washed with a small amount of 2-propanol to obtain a crystal (281 mg) containing 1:2 of (4R)—N-(1-cyanocyclopropyl)-4-(difluoro{4-[(4-methyl-piperazin-1-yl)methyl]-2-(trifluoromethyl)phenyl}methyl)-1-[(1-methylcyclopropyl)carbonyl]-L-prolinamide and succinic acid (referred to as "disuccinate" in the present specification in some cases).

Compounds of Preparation Examples and Examples shown in the following tables were prepared in the same manner as in the Preparation Examples or the Examples described above.

TABLE 3

| No. | Str |
|---|---|
| Pr1 | 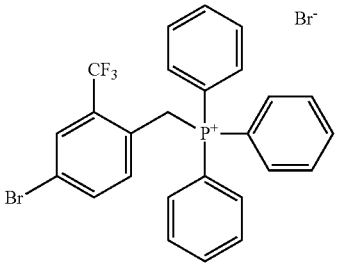 [SMILES: FC(F)(F)c1cc(Br)ccc1C[P+](c1ccccc1)(c1ccccc1)c1ccccc1 ; [Br-]] |
| Pr2/ gm | 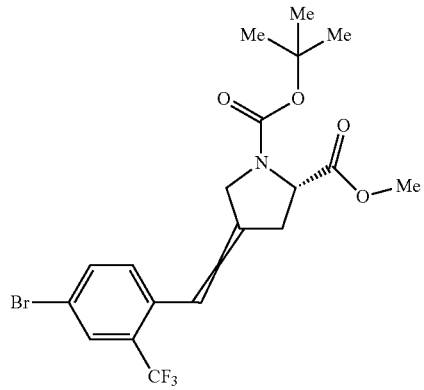 |
| Pr3/ dm | 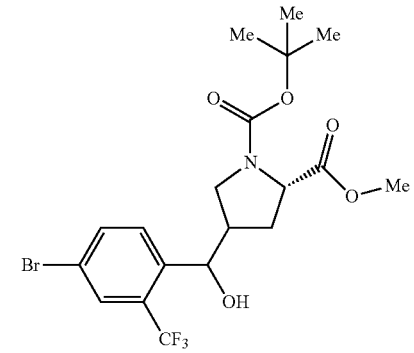 [SMILES: COC(=O)[C@@H]1CC(C(O)c2ccc(Br)cc2C(F)(F)F)CN1C(=O)OC(C)(C)C] |

TABLE 3-continued

| No. | Str |
|---|---|
| Pr3-1/ dm | 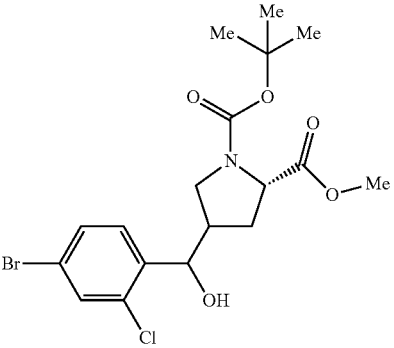 [SMILES: COC(=O)[C@@H]1CC(C(O)c2ccc(Br)cc2Cl)CN1C(=O)OC(C)(C)C] |

TABLE 4

| No. | Str |
|---|---|
| Pr3-2/ dm | 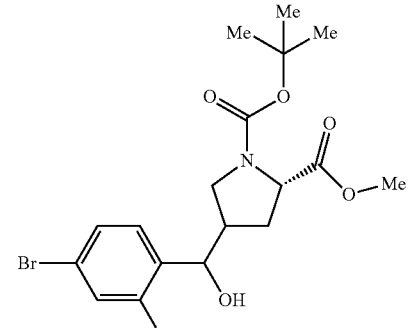 |
| Pr4/ em | 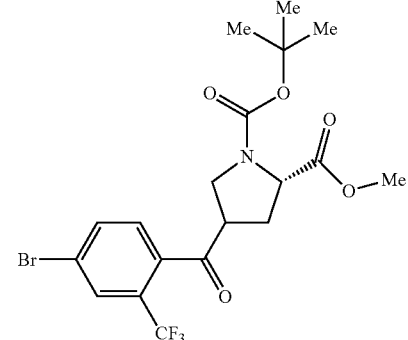 |
| Pr4-1/ em | 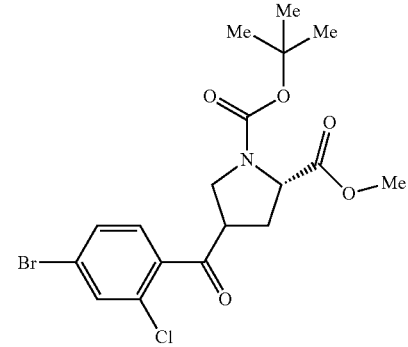 [SMILES: COC(=O)[C@@H]1CC(C(=O)c2ccc(Br)cc2F)CN1C(=O)OC(C)(C)C] |

TABLE 4-continued

| No. | Str |
|---|---|
| Pr4-2/em | (structure) |

TABLE 5

| No. | Str |
|---|---|
| Pr5/em | (structure) |
| Pr5-1/em | (structure) |
| Pr5-2/em | (structure) |

TABLE 5-continued

| No. | Str |
|---|---|
| Pr5-3/em | (structure) |

TABLE 6

| No. | Str |
|---|---|
| Pr6 | (structure) |
| Pr7 | (structure) |
| Pr7-1/em | (structure) |
| Pr7-2/em | (structure) |

TABLE 6-continued
| No. | Str |
|---|---|
TABLE 7
| No. | Str |
|---|---|
| Pr7-3/em | 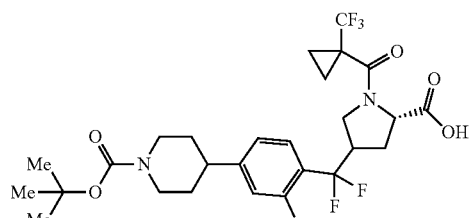 |
| Pr7-4/em | 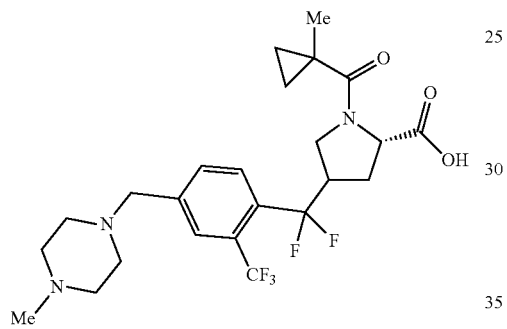 |
| Pr7-5 | 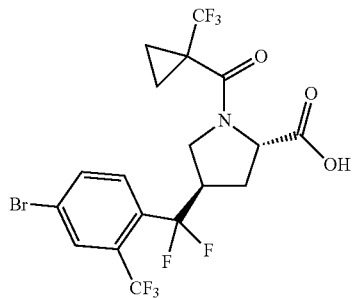 [SMILES: O=C(O)[C@@H]1C[C@@H](C(F)(F)c2ccc(Br)cc2C(F)(F)F)CN1C(=O)C1(C(F)(F)F)CC1] |
| Pr8 | 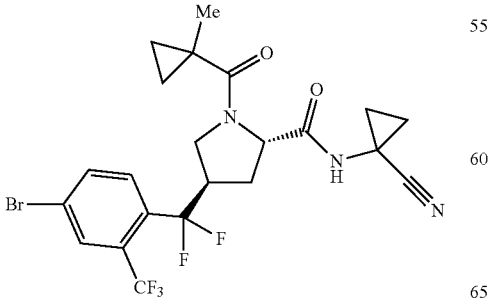 |
TABLE 8
| No. | Str |
|---|---|
| Pr8-1/em | 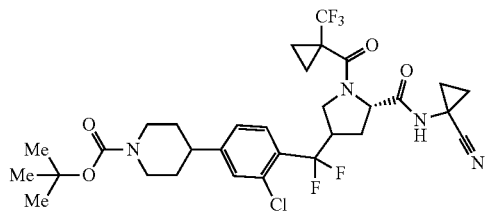 [SMILES: CC(C)(C)OC(=O)N1CCC(c2ccc(C(F)(F)C3C[C@@H](C(=O)NC4(C#N)CC4)N(C(=O)C4(C(F)(F)F)CC4)C3)c(Cl)c2)CC1] |
| Pr8-2/em | 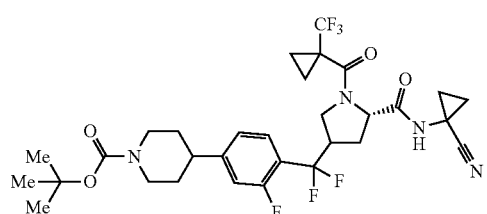 |
| Pr8-3/em | 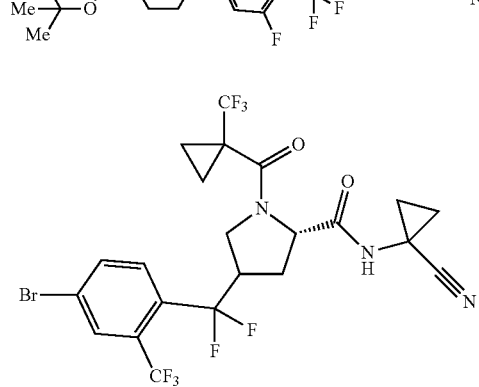 |
TABLE 9
| No. | Str |
|---|---|
| Pr8-4/em | 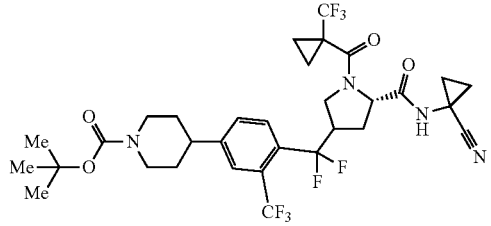 [SMILES: CC(C)(C)OC(=O)N1CCC(c2ccc(C(F)(F)C3C[C@@H](C(=O)NC4(C#N)CC4)N(C(=O)C4(C(F)(F)F)CC4)C3)c(C(F)(F)F)c2)CC1] |
| Pr8-5 | 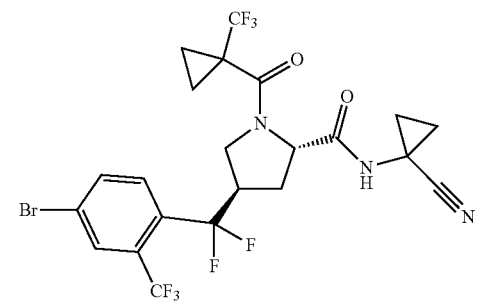 [SMILES: N#CC1(NC(=O)[C@@H]2C[C@@H](C(F)(F)c3ccc(Br)cc3C(F)(F)F)CN2C(=O)C2(C(F)(F)F)CC2)CC1] |

TABLE 9-continued
| No. | Str |
|---|---|
| Pr9/em | 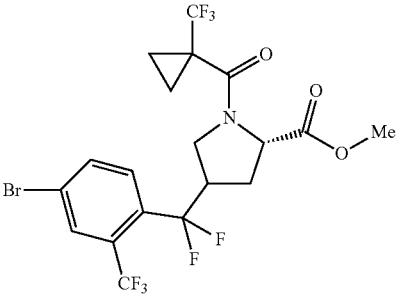 [SMILES: COC(=O)[C@@H]1CC(C(F)(F)c2ccc(Br)cc2C(F)(F)F)CN1C(=O)C1(C(F)(F)F)CC1] |
| Pr9-1/em | 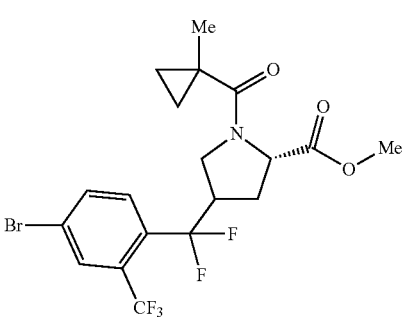 [SMILES: COC(=O)[C@@H]1CC(C(F)(F)c2ccc(Br)cc2C(F)(F)F)CN1C(=O)C1(C)CC1] |
TABLE 10
| No. | Str |
|---|---|
| Pr10 | 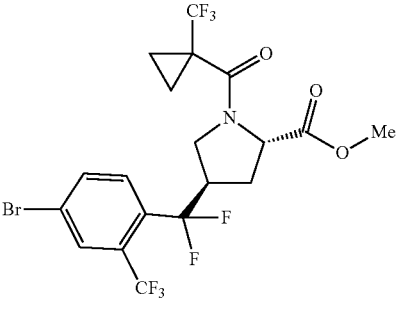 [SMILES: COC(=O)[C@@H]1C[C@@H](C(F)(F)c2ccc(Br)cc2C(F)(F)F)CN1C(=O)C1(C(F)(F)F)CC1] |
| Pr11/em | 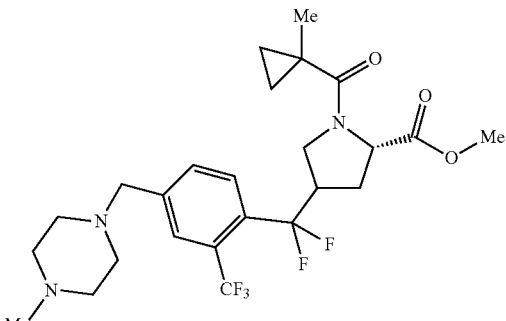 |
TABLE 10-continued
| No. | Str |
|---|---|
| Pr11-1 | 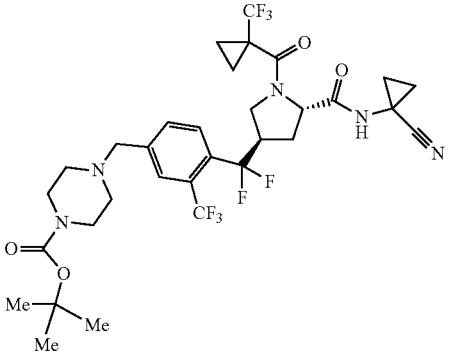 [SMILES: CC(C)(C)OC(=O)N1CCN(Cc2ccc(C(F)(F)[C@@H]3C[C@@H](C(=O)NC4(C#N)CC4)N(C(=O)C4(C(F)(F)F)CC4)C3)c(C(F)(F)F)c2)CC1] |
TABLE 11
| No. | Str |
|---|---|
| Pr11-2 | 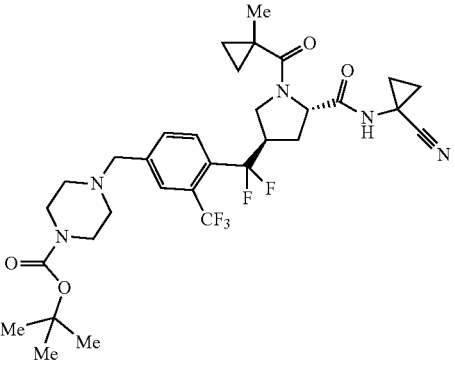 [SMILES: CC(C)(C)OC(=O)N1CCN(Cc2ccc(C(F)(F)[C@@H]3C[C@@H](C(=O)NC4(C#N)CC4)N(C(=O)C4(C)CC4)C3)c(C(F)(F)F)c2)CC1] |
| Pr12 | 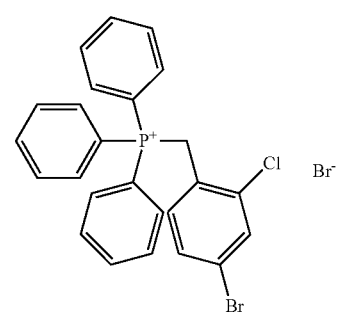 [SMILES: Fc1cc(Br)ccc1C[P+](c1ccccc1)(c1ccccc1)c1ccccc1 ; [Br-]] |
| Pr12-1 | 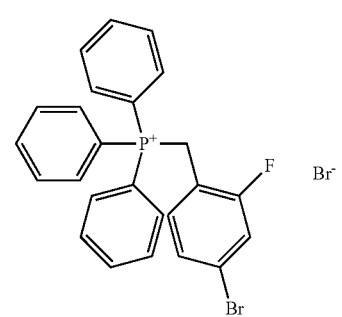 |

TABLE 12

| No. | Str |
|---|---|
| Pr13/em | (structure) |
| Pr14/em | (structure) |
| Pr15/em | (structure) |

TABLE 13

| No. | Str |
|---|---|
| Pr15-1/em | (structure) |
| Pr15-2/em | (structure) |

TABLE 13-continued

| No. | Str |
|---|---|
| Pr16/em | (structure) |
| Pr16-1/em | (structure) |

TABLE 14

| No. | Str |
|---|---|
| Pr16-2/em | (structure) |
| Pr17/gm | (structure) |
| Pr17-1/gm | (structure) |

TABLE 14-continued

| No. | Str |
|---|---|
| Pr18/em | 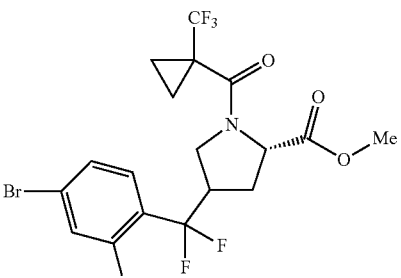 |

TABLE 15

| No. | Str |
|---|---|
| Pr18-1/em | (structure: methyl ester pyrrolidine with 1-(trifluoromethyl)cyclopropanecarbonyl on N, and CF2 linked to 4-bromo-2-fluorophenyl) |
| Pr19/em | (structure: pyrrolidine carboxylate Li+ salt with 1-(trifluoromethyl)cyclopropanecarbonyl on N, and CF2 linked to a 3-fluoro-4-(1-Boc-piperidin-4-yl)phenyl group) |

TABLE 16

| No. | Syn | Dat |
|---|---|---|
| Pr1 | Pr1 | ESI+: 501 [M]+ |
| Pr2 | Pr2 | ESI+: 488 [M + Na]+ |
| Pr3 | Pr3 | ESI+: 482 |
| Pr3-1 | Pr3 | ESI+: 450 |
| Pr3-2 | Pr3 | ESI+: 454 [M + Na]+ |
| Pr4 | Pr4 | ESI+: 502, 504 [M + Na]+ |
| Pr4-1 | Pr4 | ESI+: 468, 470 [M + Na]+ |
| Pr4-2 | Pr4 | ESI+: 432 |
| Pr5 | Pr5 | ESI+: 464 |
| Pr5-1 | Pr5 | ESI+: 466 |
| Pr5-2 | Pr5 | ESI+: 482, 484 |
| Pr5-3 | Pr5 | ESI+: 516 |
| Pr6 | Pr6 | ESI+: 486<br>NMR1: 0.48-0.59 (2H, m), 0.71-0.87 (2H, m), 1.25 (3H, s), 1.87-1.97 (1H, m), 2.24-2.35 (1H, m), 3.27-3.34 (1H, m), 3.58 (3H, s), 3.83-3.95 (2H, m), 4.38-4.47 (1H, m), 7.76 (1H, d, J = 8.5 Hz), 8.06-8.10 (1H, m), 8.11-8.13 (1H, m) |
| Pr7 | Pr7 | ESI+: 470 |
| Pr7-1 | Pr7 | ESI+: 524, 526 |
| Pr7-2 | Pr7 | ESI+: 651 [M + Na]+ |
| Pr7-3 | Pr7 | ESI+: 617, 619 [M + Na]+ |
| Pr7-4 | Pr7 | ESI+: 504 |
| Pr7-5 | Pr7 | ESI+: 526 |
| Pr8 | Pr8 | ESI+: 536 |
| Pr8-1 | Pr8 | ESI+: 681 [M + Na]+ |
| Pr8-2 | Pr8 | ESI+: 665 [M + Na]+ |
| Pr8-3 | Pr8 | ESI+: 590 |
| Pr8-4 | Pr8 | ESI+: 715 [M + Na]+ |
| Pr8-5 | Pr8 | ESI+: 588 |

TABLE 17

| No. | Syn | Dat |
|---|---|---|
| Pr9 | Pr9 | ESI+: 560 [M + Na]+ |
| Pr9-1 | Pr9 | ESI+: 486 |
| Pr10 | Pr10 | ESI+: 540 |
| Pr11 | Pr11 | ESI+: 518 |
| Pr11-1 | Pr11 | ESI+: 708 |
| Pr11-2 | Pr11 | ESI+: 654 |
| Pr12 | Pr12 | ESI+: 465, 467 [M]+ |
| Pr12-1 | Pr12 | ESI+: 449 [M]+ |
| Pr13 | Pr13 | ESI+: 734 |
| Pr14 | Pr14 | ESI+: 540 |
| Pr15 | Pr15 | ESI+: 665 [M + Na]+ |
| Pr15-1 | Pr15 | ESI+: 615 [M + Na]+ |
| Pr15-2 | Pr15 | ESI+: 631, 633 [M + Na]+ |
| Pr16 | Pr16 | ESI+: 593 |
| Pr16-1 | Pr16 | ESI+: 543 |
| Pr16-2 | Pr16 | ESI+: 559 |
| Pr17 | Pr17 | ESI+: 452, 454 [M + Na]+ |
| Pr17-1 | Pr17 | ESI+: 438 [M + Na]+ |
| Pr18 | Pr18 | ESI+: 504, 506 |
| Pr18-1 | Pr18 | ESI+: 490 |
| Pr19 | Pr19 | ESI+: 579 |

TABLE 18

| No. | Str |
|---|---|
| Ex1 | (structure: pyrrolidine-2-carboxamide with 1-methylcyclopropanecarbonyl on N, 4-CF-CF3 linked aryl bearing (4-methylpiperazin-1-yl)methyl; amide N-H to 1-cyanocyclopropyl) |
| Ex2 | (same as Ex1 as 2HCl salt) |

TABLE 18-continued
| No. | Str |
|---|---|
| Ex3/em | 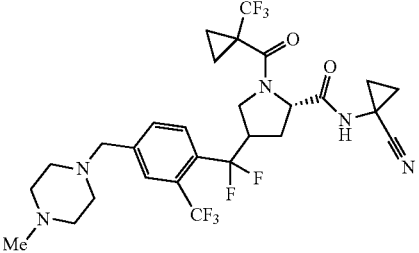 [SMILES: CN1CCN(Cc2ccc(C(F)(F)C3C[C@@H](C(=O)NC4(C#N)CC4)N(C(=O)C4(C(F)(F)F)CC4)C3)c(C(F)(F)F)c2)CC1] |
| Ex4 | 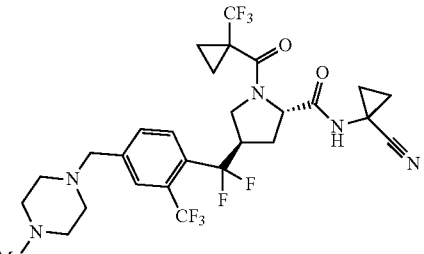 |
TABLE 19
| No. | Str |
|---|---|
| Ex5 | 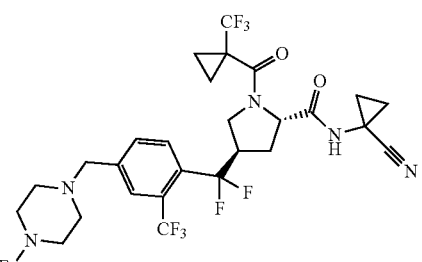 |
| Ex6 | 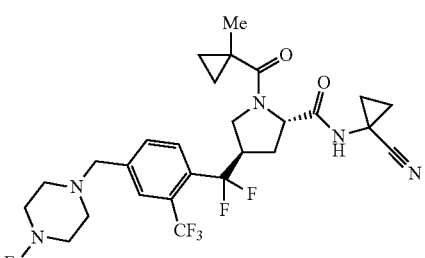 |
| Ex7 | 2HCl 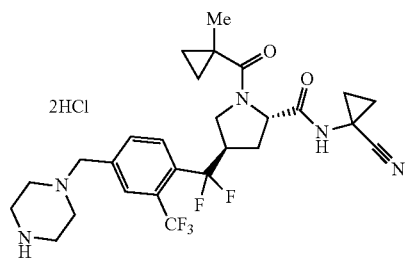 [SMILES: CC1(C(=O)N2C[C@H](C(F)(F)c3ccc(CN4CCNCC4)cc3C(F)(F)F)C[C@H]2C(=O)NC2(C#N)CC2)CC1] |
TABLE 19-continued
| No. | Str |
|---|---|
| Ex8/em | 2HCl 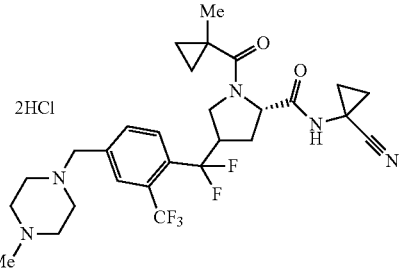 |
TABLE 20
| No. | Str |
|---|---|
| Ex9 | 2HCl 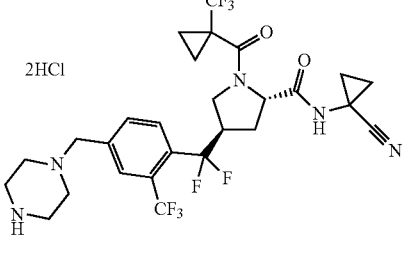 |
| Ex10/em | 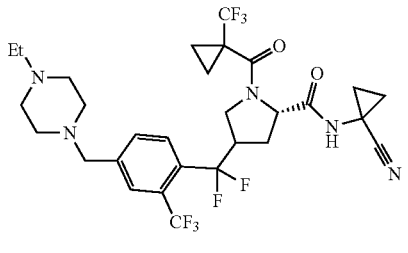 [SMILES: CCN1CCN(Cc2ccc(C(F)(F)C3C[C@@H](C(=O)NC4(C#N)CC4)N(C(=O)C4(C(F)(F)F)CC4)C3)c(C(F)(F)F)c2)CC1] |
| Ex11/em | 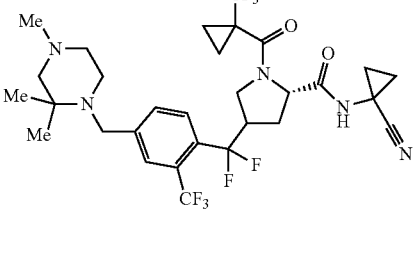 |
| Ex12 | 2HCl 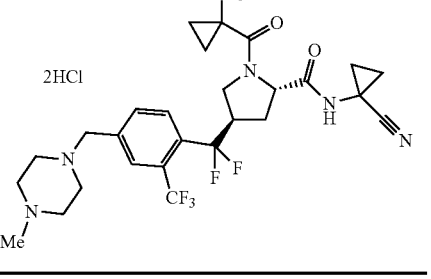 |

TABLE 21

| No. | Str |
|---|---|
| Ex13 | 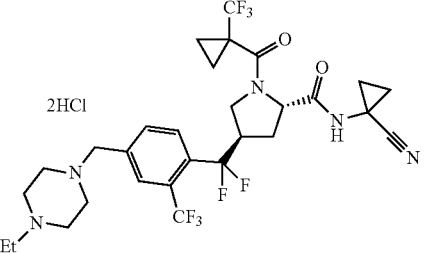 [SMILES: CCN1CCN(Cc2ccc(C(F)(F)[C@@H]3C[C@@H](C(=O)NC4(C#N)CC4)N(C(=O)C4(C(F)(F)F)CC4)C3)c(C(F)(F)F)c2)CC1] |
| Ex14 | 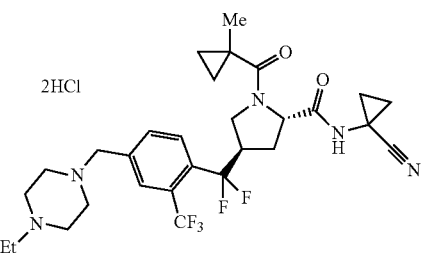 [SMILES: CCN1CCN(Cc2ccc(C(F)(F)[C@@H]3C[C@@H](C(=O)NC4(C#N)CC4)N(C(=O)C4(C)CC4)C3)c(C(F)(F)F)c2)CC1] |
| Ex15/em | 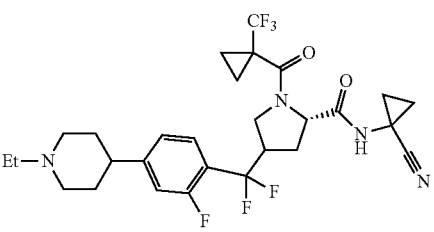 [SMILES: CCN1CCC(c2ccc(C(F)(F)C3C[C@@H](C(=O)NC4(C#N)CC4)N(C(=O)C4(C(F)(F)F)CC4)C3)c(F)c2)CC1] |
| Ex16/em | 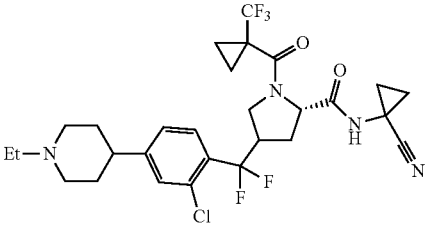 [SMILES: CCN1CCC(c2ccc(C(F)(F)C3C[C@@H](C(=O)NC4(C#N)CC4)N(C(=O)C4(C(F)(F)F)CC4)C3)c(Cl)c2)CC1] |

TABLE 22

| No. | Str |
|---|---|
| Ex17/em | 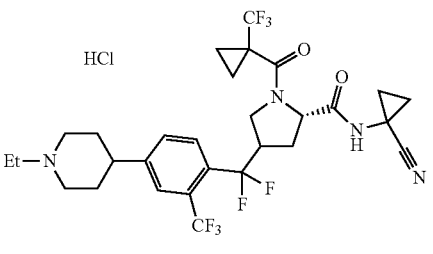 [SMILES: CCN1CCC(c2ccc(C(F)(F)C3C[C@@H](C(=O)NC4(C#N)CC4)N(C(=O)C4(C(F)(F)F)CC4)C3)c(C(F)(F)F)c2)CC1 ; Cl] |

TABLE 22-continued

| No. | Str |
|---|---|
| Ex18 | 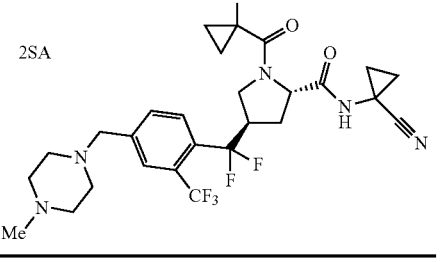 |

TABLE 23

| No. | Syn | Dat |
|---|---|---|
| Ex1 | Ex1 | ESI+: 569 |
| Ex2 | Ex2 | ESI+: 568 |
| | | NMR2: 0.46-0.54 (2H, m), 0.75-0.81 (1H, m), 0.82-0.89 (1H, m), 1.05-1.14 (2H, m), 1.23 (3H, s), 1.37-1.44 (2H, m), 1.81-1.90 (1H, m), 2.17-2.32 (1H, m), 2.75 (3H, s), 2.71-3.45 (9H, m), 3.60-4.17 (4H, m), 4.42-4.55 (1H, m), 7.76 (1H, d, J = 8.0 Hz), 7.86 (1H, d, J = 8.0 Hz), 7.98 (1H, s), 8.76 (1H, brs) |
| | | $[\alpha]_D^{23.5}$ = −21.2 (c = 1, MeOH) |
| Ex3 | Ex4 | ESI+: 623 |
| Ex4 | Ex4 | ESI+: 622 |
| Ex5 | Ex4 | ESI+: 636 |
| Ex6 | Ex4 | ESI+: 582 |
| Ex7 | Ex7 | ESI+: 554 |
| Ex8 | Ex8 | ESI+: 568 |
| Ex9 | Ex9 | ESI+: 608 |
| Ex10 | Ex10 | ESI+: 636 |
| Ex11 | Ex10 | ESI+: 650 |
| Ex12 | Ex12 | ESI+: 622 |
| | | NMR2: 1.02-1.19 (3H, m), 1.19-1.33 (3H, m), 1.34-1.48 (2H, m), 1.81-1.94 (1H, m), 2.18-2.33 (1H, m), 2.54-3.64 (9H, m), 2.75 (3H, m), 3.72-3.98 (4H, m), 4.40-4.64 (1H, m), 7.76 (1H, d, J = 8.4 Hz), 7.84 (1H, d, J = 8.4 Hz), 7.96 (1H, s), 8.83 (1H, brs) |
| Ex13 | Ex12 | ESI+: 636 |
| | | NMR2: 1.02-1.20 (3H, m), 1.21-1.31 (6H, m), 1.38-1.45 (2H, m), 1.83-1.93 (1H, m), 2.20-2.32 (1H, m), 2.76-3.24 (6H, m), 3.10 (2H, q, J = 7.6 Hz), 3.30-3.53 (3H, m), 3.61-4.32 (2H, m), 3.96 (2H, s), 4.44-4.60 (1H, m), 7.77 (1H, d, J = 8.0 Hz), 7.88 (1H, d, J = 8.4 Hz), 7.99 (1H, s), 8.85 (1H, brs) |

TABLE 24

| No. | Syn | Dat |
|---|---|---|
| Ex14 | Ex12 | ESI+: 582 |
| | | NMR2: 0.46-0.54 (2H, m), 0.73-0.81 (1H, m), 0.82-0.91 (1H, m), 1.04-1.14 (2H, m), 1.20-1.30 (6H, m), 1.37-1.45 (2H, m), 1.81-1.91 (1H, m), 2.19-2.32 (1H, m), 2.84-3.60 (9H, m), 3.11 (2H, q, J = 7.2 Hz), 3.64-3.90 (2H, m), 4.06 (2H, s), 4.14-4.82 (1H, m), 7.78 (1H, d, J = 8.0 Hz), 7.93 (1H, d, J = 7.6 Hz), 8.05 (1H, s), 8.78 (1H, brs) |
| Ex15 | Ex15 | ESI+: 571 |
| Ex16 | Ex15 | ESI+: 587, 589 |
| Ex17 | Ex17 | ESI−: 619 |
| Ex18 | Ex18 | ESI+: 568 |
| | | NMR3: 0.45-0.55 (2H, m), 0.74-0.81 (1H, m), 0.81-0.89 (1H, m), 1.02-1.11 (2H, m), 1.22 (3H, s), 1.37-1.47 (2H, m), 1.78-1.88 (1H, m), 2.17-2.30 (4H, m), 2.37-2.45 (16H, m), 2.75-3.47 (1H, m), 3.62 (2H, s), 3.65-3.89 (2H, m), 4.30-4.56 (1H, m), 7.68-7.77 (2H, m), 7.84 (1H, s), 8.73 (1H, br) |
| | | m.p.: 134.3° C. |
| | | 2θ: 2.7, 5.3, 9.8, 10.4, 13.5, 14.0, 15.1, 16.6, 17.4, 24.4° |

INDUSTRIAL APPLICABILITY

The phenyldifluoromethyl-substituted prolinamide compound of the present invention has the cathepsin S inhibitory effect and is expected as an agent for preventing and/or treating autoimmune disease including SLE and lupus nephritis, allergies, or graft rejection of an organ, bone marrow or tissue.

The invention claimed is:

1. A compound or a salt thereof, which is selected from the group consisting of:
   (4R)—N-(1-cyanocyclopropyl)-4-(difluoro{4-[(4-methylpiperazin-1-yl)methyl]-2-(trifluoromethyl)phenyl}methyl)-1-[(1-methylcyclopropyl)carbonyl]-L-prolinamide,
   (4R)—N-(1-cyanocyclopropyl)-4-(difluoro{4-[(4-methylpiperazin-1-yl)methyl]-2-(trifluoromethyl)phenyl}methyl)-1-{[1-(trifluoromethyl)cyclopropyl]carbonyl}-L-prolinamide,
   (4R)—N-(1-cyanocyclopropyl)-4-[{4-[(4-ethylpiperazin-1-yl)methyl]-2-(trifluoromethyl)phenyl}(difluoro)methyl]-1-{[1-(trifluoromethyl)cyclopropyl]carbonyl}-L-prolinamide,
   (4R)—N-(1-cyanocyclopropyl)-4-[{4-[(4-ethylpiperazin-1-yl)methyl]-2-(trifluoromethyl)phenyl}(difluoro)methyl]-1-[(1-methylcyclopropyl)carbonyl]-L-prolinamide, and
a salt thereof.

2. The compound or a salt thereof according to claim 1, which is (4R)—N-(1-cyanocyclopropyl)-4-(difluoro{4-[(4-methylpiperazin-1-yl)methyl]-2-(trifluoromethyl)phenyl}methyl)-1-[(1-methylcyclopropyl)carbonyl]-L-prolinamide or a salt thereof.

3. The compound or a salt thereof according to claim 1, which is (4R)—N-(1-cyanocyclopropyl)-4-(difluoro {4-[(4-methylpiperazin-1-yl)methyl]-2-(trifluoromethyl)phenyl}methyl)-1-{[1-(trifluoromethyl)cyclopropyl]carbonyl}-L-prolinamide or a salt thereof.

4. The compound or a salt thereof according to claim 1, which is (4R)—N-(1-cyanocyclopropyl)-4-[{4-[(4-ethylpiperazin-1-yl)methyl]-2-(trifluoromethyl)phenyl}(difluoro)methyl]-1-{[1-(trifluoromethyl)cyclopropyl]carbonyl}-L-prolinamide or a salt thereof.

5. The compound or a salt thereof according to claim 1, which is (4R)—N-(1-cyanocyclopropyl)-4-[{4-[(4-ethylpiperazin-1-yl)methyl]-2-(trifluoromethyl)phenyl}(difluoro)methyl]-1-[(1-methylcyclopropyl)carbonyl]-L-prolinamide or a salt thereof.

6. A pharmaceutical composition comprising the compound or a salt thereof according to claim 1, and one or more excipients.

* * * * *